US012617864B2

(12) United States Patent
Seong et al.

(10) Patent No.: US 12,617,864 B2
(45) Date of Patent: May 5, 2026

(54) METHODS OF ACTIVATING AND PROLIFERATING EXHAUSTED CD8 T CELLS, CD8 T CELLS WITH ENHANCED ACTIVITY PREPARED BY THE SAME, AND USES THEREOF

(71) Applicant: Medgene Therapeutics, Inc., Silver Spring, MD (US)

(72) Inventors: Rho Hyun Seong, Seongnam-si (KR); Jin Woo Nah, Seoul (KR)

(73) Assignee: Medgene Therapeutics, Inc., Silver Spring, MD (US)

( * ) Notice: Subject to any disclaimer, the term of this patent is extended or adjusted under 35 U.S.C. 154(b) by 1056 days.

(21) Appl. No.: 17/718,551

(22) Filed: Apr. 12, 2022

(65) Prior Publication Data

US 2022/0332841 A1     Oct. 20, 2022

Related U.S. Application Data

(63) Continuation-in-part of application No. 17/478,445, filed on Sep. 17, 2021, now abandoned.

(30) Foreign Application Priority Data

Apr. 12, 2021     (KR) ........................ 10-2021-0047002

(51) Int. Cl.

| | |
|---|---|
| *C07K 16/30* | (2006.01) |
| *A61K 38/00* | (2006.01) |
| *A61K 40/11* | (2025.01) |
| *A61K 40/31* | (2025.01) |
| *A61K 40/32* | (2025.01) |
| *A61K 40/42* | (2025.01) |
| *A61P 35/00* | (2006.01) |
| *C07K 14/705* | (2006.01) |
| *C07K 14/725* | (2006.01) |
| *C12N 15/67* | (2006.01) |
| *C12N 15/86* | (2006.01) |

(52) U.S. Cl.
CPC .............. *C07K 16/30* (2013.01); *A61K 40/11* (2025.01); *A61K 40/31* (2025.01); *A61K 40/32* (2025.01); *A61K 40/4242* (2025.01); *A61K 40/4254* (2025.01); *A61K 40/4266* (2025.01); *A61K 40/4273* (2025.01); *A61P 35/00* (2018.01); *C07K 14/7051* (2013.01); *C07K 14/70517* (2013.01); *C07K 14/70521* (2013.01); *C12N 15/67* (2013.01); *C12N 15/86* (2013.01); *A61K 38/00* (2013.01); *A61K 2239/13* (2023.05); *A61K 2239/31* (2023.05); *A61K 2239/38* (2023.05); *C07K 2317/622* (2013.01); *C07K 2319/02* (2013.01); *C07K 2319/03* (2013.01); *C07K 2319/33* (2013.01); *C12N 2740/10043* (2013.01); *C12N 2740/15043* (2013.01)

(58) Field of Classification Search
CPC ...................................................... C07K 16/30
See application file for complete search history.

(56) References Cited

U.S. PATENT DOCUMENTS

| | | |
|---|---|---|
| 8,106,092 B2 | 1/2012 | Ogbourne et al. |
| 2013/0078226 A1 | 3/2013 | Nakauchi et al. |
| 2016/0009813 A1 | 1/2016 | Themeli et al. |
| 2019/0218515 A1 | 7/2019 | Ballesteros Nobell et al. |

FOREIGN PATENT DOCUMENTS

| | | |
|---|---|---|
| JP | 2018531612 A | 11/2018 |
| JP | 2018533363 A | 11/2018 |
| KR | 1020200113284 | 2/2014 |
| KR | 1020160058960 | 10/2014 |
| KR | 1020170074245 | 10/2015 |
| KR | 1020190111843 | 10/2019 |
| KR | 1020200027508 | 3/2020 |
| WO | 2011096482 A1 | 8/2011 |
| WO | 2020027094 A1 | 2/2020 |
| WO | 2020200303 A1 | 10/2020 |

OTHER PUBLICATIONS

Yamada et al., "The transcription factor ELF4 controls the proliferation and homing of CD8+ T cells via the Krüppel-like factors KLF4 and KLF2". Nat Immunol. Jun. 2009;10(6):618-26 (Year: 2009).*

Mamonkin, et al., "Differential roles of KLF4 in the development and differentiation of CD8+ T cells". Immunology Letters, vol. 156, Issues 1-2, 2013, pp. 94-101 (Year: 2013).*

Wherry et al., "Molecular Signature of CD8+ T Cell Exhaustion during Chronic Viral Infection". Immunity. vol. 27, Issue 4. pp. 670-684. Oct. 26, 2007 (Year: 2007).*

(Continued)

*Primary Examiner* — Christopher M Babic

*Assistant Examiner* — Hanan Isam Abuzeineh

(74) *Attorney, Agent, or Firm* — Potomac Law Group, PLLC; Judith U. Kim

(57)     ABSTRACT

The present invention relates to a method for activating a cell and a cell activated thereby and a use thereof, more particularly, to an in vitro method of enhancing, recovering of immune response of CD8 T cells in exhaustion and proliferating the CD8 T cells comprising the step of inducing overexpression of Klf4 protein in CD8 T cells, a cell population containing the CD8 T cells or transduced CAR-CD8 T cells whose anticancer activity is enhanced by overexpressing Klf4 protein and use thereof.

42 Claims, 14 Drawing Sheets

Specification includes a Sequence Listing.

(56)        References Cited

OTHER PUBLICATIONS

An, J. et al., "Role of Krüppel-like factor 4 (Klf4) in regulation of T cell No. and TH-17 differentiation (139.12)", J. Immunol. 184:139. 12 (Apr. 2010).

Di Tomaso, E. et al., "Abstract A26: Detecting PIK3CA mutations in circulating cell-free DNA from patients with metastatic cancer: An exploratory analysis in patientswith endometrial and lung cancer, p13k-mtor activation in human cancer," Molecular Cancer Therapy 14: A26 (Jul. 2015).

Extended Search Report issued in EP 22788269.3, mailed on Mar. 4, 2025.

Gattinoni, L. et al., "Paths to stemness: building the ultimate antitumour T cell," Nat. Rev. Cancer 12:671-684 (Oct. 2012).

Hartmann, J. et al., "Clinical development of CAR T cells—challenges and opportunities in translating innovative treatment concepts," EMBO Molecular Medicine 9:1-15 (Aug. 2017).

Li, K. et al., "Klf4 reduces stemness phenotype, triggers mesenchymal-epithelial transition (MET)-like molecularchanges, and prevents tumor progression in nasopharygeal carcinoma," Oncotarget 8:93924-93941 (Sep. 2017).

Nishimura, T. et al., "Generation of Rejuvenated Antigen-Specific T Cells by Reprogramming to Pluripotency and Redifferention," Cell Stem Cell 12:114-126 (Jan. 2013).

Patel, S. et al., "Induced Pluripotent Stem Cell-derived T cells for Cancer Immunotherapy," Surg. Oncol. Clin. No. Am. 28:489-504 (pp. 1-21) (Jul. 2019).

Shan, Q. et al., "Ectopic Tcf1 expression instills a stem-like program in exhausted CD8+ T cells to enhance viral and tumor immunity," Cellular & Molecular Immunology 18:1262-1277 (Apr. 2020).

Themeli, M. et al., "Generation of tumor-targeted human T lymphocytes from induced pluripotent stem cells for cancer therapy," Nature Biotechology 31:928-933 and 2678 (2 pages) (Oct. 2013).

Vizcardo, R. et al., "Regeneration of Human Tumor Antigen-Specific T Cells from iPSCs Derived from Mature CD8+ T Cells," Cell Stem Cell 12:31-36 (Jan. 2013).

Waugh, K.A. et al., "Targeting Transcriptional Regulators of CD8+ T Cell Dysfunction to Boost Anti-Tumor Immunity," Vaccines 3:771-802 (Aug. 2015).

Wen, X. et al., "Downregulation of the transcription factor KLF4 is required for the lineage commitment of T cells," Cell Research 21:1701-1710 (pub'd online Nov. 2011).

Wu, Y. et al., "Overexpression of Kruppel-Like Factor 4 Suppresses Migration and Invasion of Non-Small Cell Lung Cancer Through c-Jun-NH2-Terminal Kinase/Epithelial-Mesenchymal Transition Signaling Pathway," Frontiers in Pharmacology 10:1512 (16 pages) (Jan. 2020).

* cited by examiner

Rag2 KO mice

D-0                    D+1                    Day15
                                              Analysis MC38-gp100            MigRI/Klf4
(3x10$^5$)            CD8 T cells
                      (1x10$^6$)

Klf4 mRNA

Klf4 mRNA

METHODS OF ACTIVATING AND PROLIFERATING EXHAUSTED CD8 T CELLS, CD8 T CELLS WITH ENHANCED ACTIVITY PREPARED BY THE SAME, AND USES THEREOF

CROSS-REFERENCES TO RELATED APPLICATIONS

This application is a continuation-in-part of U.S. application Ser. No. 17/478,445, filed Sep. 17, 2021, which claims priority to KR Appl. No. 10-2021-0047002, filed Apr. 12, 2021, both of which are incorporated herein by reference in their entirety.

REFERENCE TO SEQUENCE LISTING SUBMITTED ELECTRONICALLY

The content of the electronically submitted sequence listing in ASCII text file (Name: 2486-0003US02_Sequence Listing_ST25. txt; Size: 25.4 KB; and Date of Creation: Apr. 12, 2022) filed with the application is incorporated herein by reference in its entirety.

TECHNICAL FIELD

The present invention relates to a method of cell proliferation and activation, a cell activated thereby and a use thereof, and more particularly, to a method of activating and proliferating CD8 T cells continuously exposed to an antigen, and CD8 T cells with enhanced anticancer activity produced by the same and uses thereof.

BACKGROUND OF THE INVENTION

Most CD8 T cells infiltrated the tumor tissue recognize specific antigens derived from cancer cells. The antigen (Ag)-activated CD8 T cells can eliminate cancer cells by secreting effector molecules such as granzyme B, interferon-gamma (IFN-γ), and perforin. Therefore, increasing the activity of the CD8 T cells specific for cancer antigens is regarded as one of the most efficient approaches to treat cancers. Check point inhibitors such as anti-PD-1 and anti-CTLA antibodies (Abs) work to control cancers in such a way, however, the efficiency is quite limited. It is recognized that controlling the CD8 T cell activity in cancer tissues is highly sophisticated because of the complex characteristics of cancer microenvironment.

In the cancer microenvironment, antigen-specific CD8 T cells are continuously exposed to cancer antigens unless cancer is completely removed. Chronic antigen stimulation makes CD8 T cells fall into unresponsive state which is currently described as 'exhaustion'. Exhausted CD8 T cells are not able to efficiently eliminate cancer cells because they cannot perform a normal immune response due to the weakening of active cytokine secretion and cell division functions. In particular, these exhausted CD8 T cells have a characteristic that they do not easily return to cells with normal functions even after time passes. Therefore, preventing CD8 T cells from being exhausted in the tumor tissue and reactivating the function of the exhausted cells is critical to control cancers.

Recent studies have shown that CD8 T cells from chronic virus infected tissues or tumor tissues are composed of 4 subsets of cell groups displaying stages of exhaustion; These include chronic progenitor cell subset (Progenitor exhausted cells 1, Progenitor exhausted cells 2), chronic effector cell subset (intermediate exhausted cells) and end-stage exhausted cell subset (terminal exhausted cells). Among them, chronic effector cell subset has the highest effector function to recognize and remove cancer cells, but terminal exhausted cells are known to have lost a significant part of an effector function. Indeed, it is known that most of the CD8 T cells present in cancer tissues do not function properly since they are in the terminal state of exhaustion. Therefore, if a method for enhancing the generation and function of chronic effector cells from cancer-specific CD8 T cells is developed, it will be very useful to effectively control and treat cancer.

With respect to anticancer treatment using CD8 T cells, U.S. Pat. No. 8,106,092 discloses a method of treating secondary cancer by inducing necrosis of cancer cells and promoting generation of cancer-specific T cells such as CD8 T cells, comprising administrating ingenol-3-angelate locally and/or intratumorally to an individual with secondary cancer, and US Patent Publication No. US20190218515A discloses a method of producing activated T cells comprising treating T cells isolated from cancer patients with a dual specific antibody against CD123/CD3, a dual-specific antibody against CD19/CD3 or a dual-specific antibody against EpCAM/CD3.

On the other hand, T cell therapeutics are being developed up to the 3rd generation so far. The first-generation T cell therapeutics have low specificity for cancer cells because they are administered to patients by proliferating all T cells (bulk T cells) present in the blood or cancer tissue. Efficacy could not be expected, and the second-generation T cell therapeutics showed an improved therapeutic effect by isolating/mass-culturing only tumor antigen-specific T cells and administering them to cancer patients. The problem of this long and complicated process has been raised, and the third-generation T cell therapeutics have been developed by either 1) directly introducing a TCR gene that recognizes a specific cancer antigen into T cells, or 2) preparing a fusion protein by linking an antigen recognition site (scFv) of a monoclonal antibody that recognizes a specific antigen to a T cell activation domain and then introducing the fusion protein into T cells, and thereby increased antigen specificity and shortening the manufacturing period, and the therapeutic efficacy is also very good, close to 100% treatment in case of some leukemias and lymphomas. The second type of third-generation T cell therapy is characterized by being genetically engineered to express the so-called chimeric antigen receptor (hereinafter, abbreviated as "CAR").

The leading companies based on the CAR-introduced T-cell technology are Novartis, Juno Therapeutics, and Kite Pharma of the United States, all of which have developed CAR-introduced T cells that target CD19, a B-cell-specific antigen. The CAR-T cell therapeutics developed by the companies showed a high therapeutic effect of 80 to 90% in resistant/recurrent acute lymphoblastic lymphomas (ALL) and non-Hodgkin's lymphoma (NHL), while positioning them as leaders in targeted immune cell therapies (Hartmann et al., *EMBO Mol. Med.* 9 (9): 1183-1197, 2017). Furthermore, one of the world's first chimeric antigen receptor T-cell (CAR-T) therapeutics, 'Cymriaju' (Indgredient Name: Tisagen Lexel) recently applied for approval by Novartis Korea, was approved as the No. 1 high-tech biopharmaceutical in accordance with Advanced Regenerative Bio Act of Korea.

SUMMARY OF THE INVENTION

However, the prior technologies also have limitations in that they do not take into account the phenomenon of CD8

T cells being exhausted in the body and do not aim to utilize these specialized cells or to overcome this condition.

The present invention is to solve various problems related to T cell exhaustion including the above problems in T cell immunotherapy. Thus, the object of the present invention is to provide a method and composition capable of controlling cancer by regulating the exhaustion process of CD8 T cells in vivo. However, these problems are exemplary and do not limit the scope of the present invention.

In an aspect of the present invention, there is provided an in vitro method of suppressing the exhaustion state of CD8 T cells comprising inducing overexpression of Klf4 protein in CD8 T cell-containing cells selected from the group consisting of a) CD8 T cells, b) a cell population comprising the CD8 T cells, and c) transduced CAR-CD8 T cells prepared by transducing the CD8 T cells with a gene encoding a chimeric antigen receptor (CAR).

In another aspect of the present invention, there is provided an in vitro method of enhancing immune response of CD8 T cells comprising inducing overexpression of Klf4 protein in CD8 T cell-containing cells selected from the group consisting of a) CD8 T cells, b) a cell population comprising the CD8 T cells, and c) transduced CAR-CD8 T cells prepared by transducing the CD8 T cells with a gene encoding a chimeric antigen receptor (CAR).

In another aspect of the present invention, there is provided an in vitro method of proliferating CD8 T cells isolated from a subject comprising inducing overexpression of Klf4 protein in CD8 T cell-containing cells selected from the group consisting of a) CD8 T cells, b) a cell population comprising the CD8 T cells, and c) transduced CAR-CD8 T cells prepared by transducing the CD8 T cells with a gene encoding a chimeric antigen receptor (CAR).

In another aspect of the present invention, there is provided a pharmaceutical composition for treating cancer comprising CD8 T cell-containing cells whose expression of Klf4 is induced selected from the group consisting of: a) CD8 T cells isolated from a subject, b) a cell population containing the CD8 T cells, c) CAR-CD8 T cells prepared by transducing the CD8 T cells or the cell population with a gene construct encoding a chimeric antigen receptor as an active ingredient.

In another aspect of the present invention, there is provided a transformed CD8 T cell transduced to overexpress Klf4 protein.

In another aspect of the present invention, there is provides a transformed CAR-CD8 T cell transduced to overexpress Klf4 protein and a chimeric antigen receptor (CAR)

In another aspect of the present invention, there is provided a method of treating a subject suffering from cancer comprising: preparing cells selected from the group consisting of a) CD8 T cells isolated from the subject, b) a cell population comprising the CD8 T cells, and a CAR-CD8 T cell prepared by transducing the CD8 T cells with a gene encoding a CAR; inducing overexpression of Klf4 protein in the cells by transducing the cells with a polynucleotide encoding the Klf4 protein or treating the cells with a Klf4 inducer; and administrating the CD8 T cells, the cell population comprising the CD8 T cells, or the CAR-CD8 T cell whose overexpression of Klf4 protein is induced to the subject.

In another aspect of the present invention, there is provided a method of treating cancer in a subject comprising: preparing induced CD8 T cells overexpressing Klf4 protein or transduced CAR-CD8 T cells expressing Klf4 protein; and administrating the induced CD8 T cells or transduced CAR-CD8 T cells to the subject. In another aspect of the present invention, there is provided a method of treating cancer in a subject comprising: inducing overexpression of Klf4 protein in the cells selected from the group consisting of a) CD8 T cells isolated from the subject, b) a cell population comprising the CD8 T cells, and a CAR-CD8 T cell prepared by transducing the CD8 T cells with a gene encoding a CAR; and administrating the cells whose overexpression of Klf4 protein induced to the subject.

In another aspect of the present invention, there is provided a composition comprising transformed CD8 T cells transduced to overexpress Klf4 protein or a transformed CAR-CD8 T cells transduced to overexpress Klf4 protein and a chimeric antigen receptor (CAR).

EFFECTS OF THE INVENTION

As described above, the method according to an embodiment of the present invention can be usefully used in the development of more efficient anticancer cell therapeutics by preventing the exhaustion of immune cells.

BRIEF DESCRIPTION OF DRAWINGS

Figures 1A, 1B:
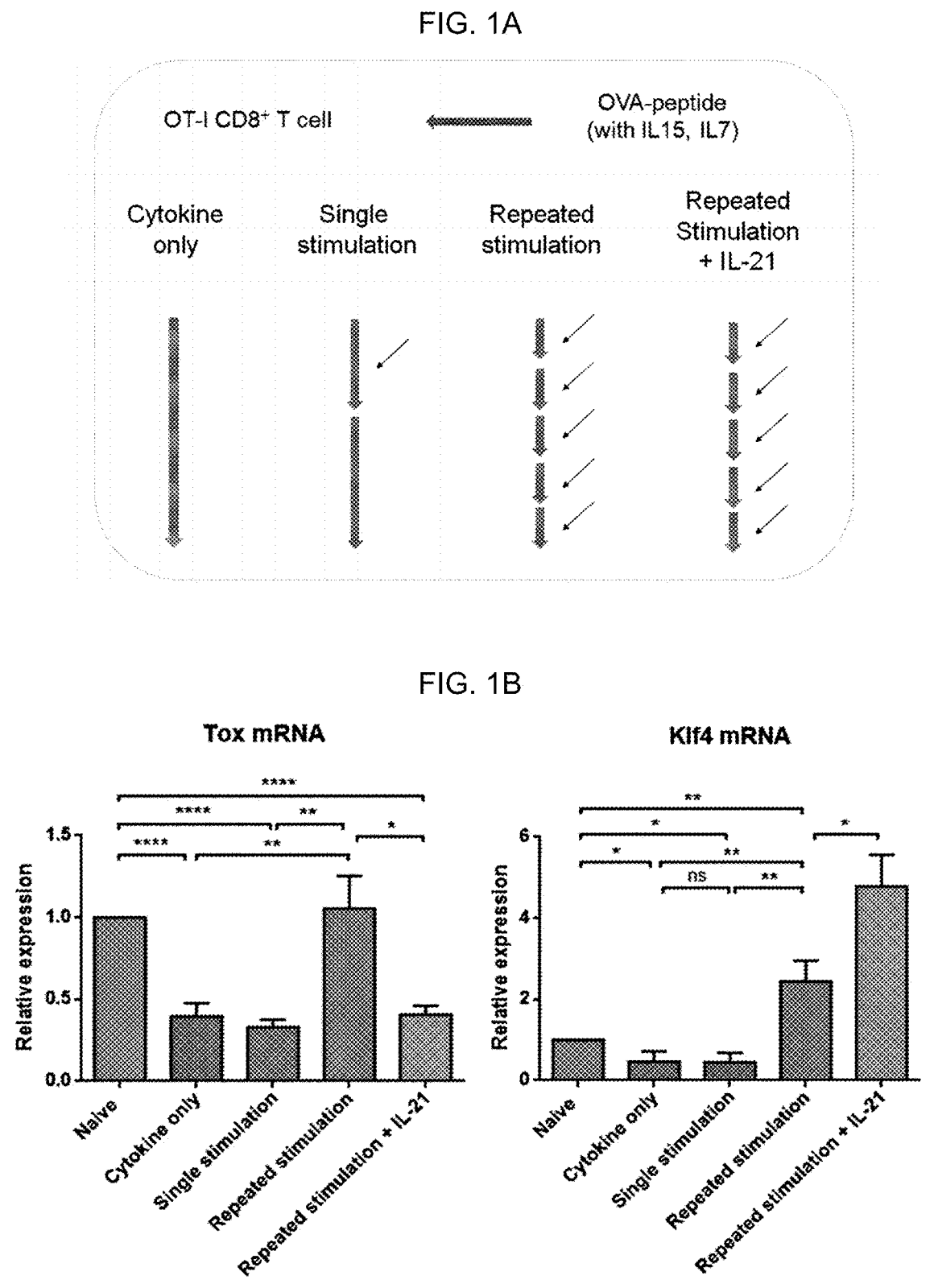

FIG. 1A is a schematic diagram schematically showing the design of a repeated stimulation test for antigen on CD8 T cells according to an embodiment of the present invention; FIG. 1B is a series of graphs showing the results of measuring the expression level at the mRNA level of Tox (left) and Klf4 (right), markers related to the exhaustion state of CD8 T cells showing experimental results performed according to the experimental design of FIG. 1A.

FIG. 2A shows a series of histograms (left) representing the result of FACS analyses on CD8 T cells transformed with a control retroviral vector (MigRI) or CD8 T cells transformed with a retroviral vector (Klf4) using markers specific to aforementioned subsets and a graph (right) representing the result of the FACS analyses; FIG. 2B shows a histogram (left) representing ratio of dead cancer cells when cultivating CD8 T cells transformed with control (MigRI) vector or the Klf4 gene with target cancer cells and a graph quantifying the FACS results; FIG. 2C is a series of graphs representing the results of measuring gene expression level of Klf4 (left) and Tox (right) at the mRNA level in the control (MigRI) and CD8 T cells transformed with the Klf4 gene; FIG. 2D shows a series of histograms (left) representing FACS analyses showing the proportion of CD8 T cells expressing granzyme B (GzmB) in four groups of CD8 T cells (clockwise from top left, MigRI-GFP$^-$, MigRI-GFB$^+$, Klf4-GFP$^+$, Klf4-GFP$^-$) and a graph (right) quantifying the FAC analyses; and FIG. 2E shows a series of histograms (left) representing FACS analyses showing the proportion of CD8 T cells expressing interferon-γ (INF-γ), which has a key role in the function of CD8 T cells in four groups of CD8 T cells (clockwise from top left, MigRI-GFP$^-$, MigRI-GFP$^+$, Klf4-GFP$^+$, Klf4-GFP$^-$) and a graph (right) quantifying the FACS analyses.

DETAILED DESCRIPTION OF THE INVENTION

Figure 1C:
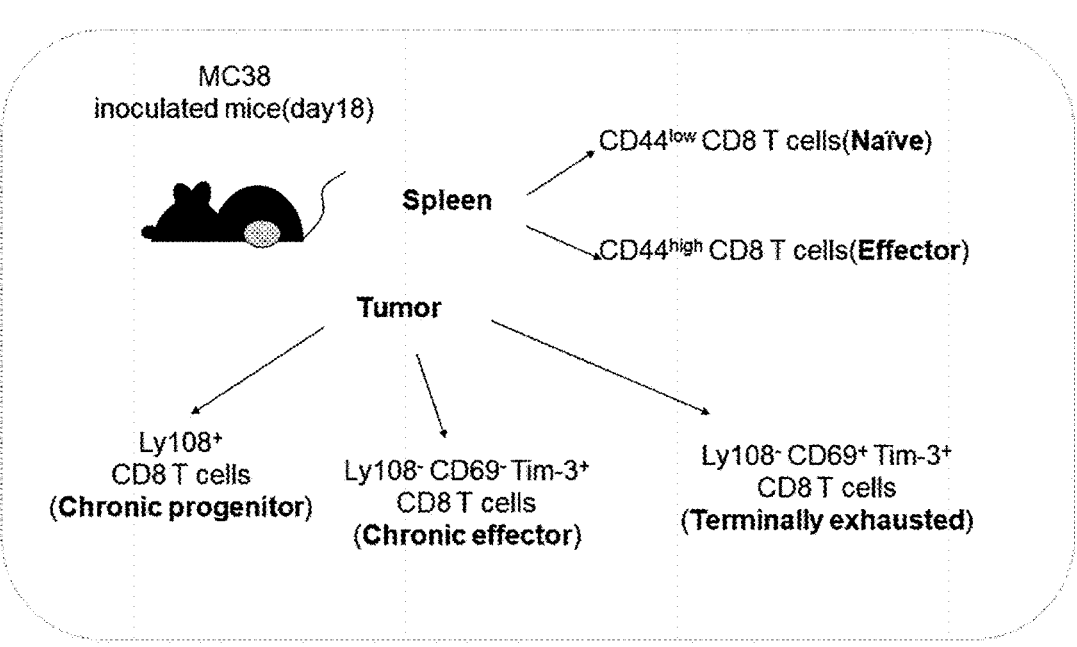
FIG. 1c is a schematic diagram representing the marker phenotypes for various stages of CD8 T cell subsets from spleen and from tumor tissue induced by inoculating MC38 colon cancer cells into mice.

In an aspect of the present invention, there is provided an in vitro method of suppressing the exhaustion state of CD8 T cells comprising inducing overexpression of Klf4 protein in the cells selected from the group consisting of a) CD8 T cells isolated from a subject, b) a cell population comprising the CD8 T cells, and c) CAR-CD8 T cells prepared by transducing the CD8 T cells with a gene encoding a chimeric antigen receptor (CAR).

In another aspect of the present invention, there is provided an in vitro method of enhancing immune response of CD8 T cells comprising inducing overexpression of Klf4 protein in the cells selected from the group consisting of a) CD8 T cells isolated from a subject, b) a cell population comprising the CD8 T cells, and c) CAR-CD8 T cells prepared by transducing the CD8 T cells with a gene encoding a chimeric antigen receptor (CAR).

In another aspect of the present invention, there is provided an in vitro method of proliferating CD8 T cells isolated from a subject comprising inducing overexpression of Klf4 protein in the cells selected from the group consisting of a) CD8 T cells isolated from a subject, b) a cell population comprising the CD8 T cells, and c) CAR-CD8 T cells prepared by transducing the CD8 T cells with a gene encoding a chimeric antigen receptor (CAR).

In the method, the overexpression of the Klf4 protein is performed by transfecting the CD8 T cell with an expression vector containing a polynucleotide encoding the Klf4 protein, or introducing the Klf4 proteins, or introducing an mRNA expressing the Klf4 protein into the CD8 T cell or treating the CD8 T cells with a Klf4 inducer. The Klf4 protein can comprise an amino acid sequence represented by SEQ ID Nos: 4 or 5. In addition, the polynucleotide encoding the Klf4 protein can comprise a nucleotide sequence represented by SEQ ID Nos: 1 or 6. However, the present invention is not limited thereto. Any other Klf4 proteins or polynucleotides encoding the same can be used. Preferably, Klf4 protein or polynucleotides encoding the same derived from mammals, particularly from primates such as chimpanzees, gorillas, orangutans, gibbons, cynomolgus monkeys, and rhesus monkeys can be used.

In the method, the expression vector can be a viral vector or a non-viral vector, and the viral vector can be an adeno-associated virus (AAV) vector, an adenovirus vector, an alphavirus vector, a herpes simplex virus vector, or a vaccinia virus vector, Sendaivirus vector, flavivirus vector, radovirus vector, retroviral vector, herpesvirus vector, poxvirus vector or lentiviral vector. In the method, the non-viral vector can be a DNA vector, nanoparticles, cationic polymer, exosome, extracellular vesicle or liposome, and the DNA vector can be a plasmid vector, a cosmid vector, a phagemid vector, or an artificial human chromosome.

The expression vector can include an appropriate regulatory sequence linked to a polynucleotide encoding the Klf4 protein so that the Klf4 protein can be overexpressed in the CD8 T cell, wherein the construction sequence is operably linked to the polynucleotide. In this case, it can be referred to as a "gene construct" by integrating the regulatory sequence and a polynucleotide encoding the Klf4 protein operably linked thereto. The gene construct can include appropriate restriction enzyme recognition sites at both ends for cloning in an expression vector.

As used herein, the term "operably linked to" refers to a nucleic acid sequence of interest (e.g., in an in vitro transcription/translation system or in a host cell) is linked to a regulatory sequence in such a way that its expression can be achieved. The term "regulatory sequence" includes promoters, enhancers and other regulatory elements (e.g., polyadenylation signals). Regulatory sequences include constitutive elements directing that a target nucleic acid can be constitutively expressed in various host cells, inducible elements directing that a target nucleic acid can be expressed only in specific tissues or cells (e.g., tissue-specific regulatory sequences). It can be understood by those skilled in the art that the design of the expression vector can vary depending on factors such as the selection of the host cell to be transformed and the level of desired protein expression. The regulatory sequences enabling expression in eukaryotic and prokaryotic cells are well known to those skilled in the art. As described above, they usually contain regulatory sequences responsible for initiation of transcription and, optionally, poly-A signals responsible for termination and stabilization of the transcript. Additional regulatory sequences can include, in addition to transcriptional regulators, translation enhancers and/or natively combined or heterologous promoter regions. Possible regulatory sequences enabling expression in, for example, mammalian host cells are the CMV-HSV thymidine kinase promoter, SV40, RSV-promoter (Rous sarcoma virus), human kidney element 1α-promoter, glucocorticoid-inducible MMTV (mouse mammary tumor virus)-promoters, metallothionein-inducible promoter or tetracycline-inducible promoters, or amplifying agents such as CMV amplifiers or SV40 amplifiers. For expression in neurons, it is contemplated that neurofilament-promoter, PGDF-promoter, NSE-promoter, PrP-promoter or thy-1-promoter can be used. Such promoters are known in the art and are described in documents (Charron et al., *J. Biol. Chem.* 270: 25739-25745, 1995, etc.). For expression in prokaryotic cells, a number of promoters have been disclosed, including the lac-promoter, the tac-promoter or the trp promoter. In addition to factors capable of initiating transcription, the regulatory sequences include transcription termination signals such as SV40-poly-A site or TK-poly-A site downstream of the polynucleotide according to an embodiment of the present invention. Suitable expression vectors are known in the art, such as Okayama-Berg cDNA expression vectors pcDV1 (Parmacia), pRc/CMV, pcDNA1, pcDNA3 (Invitrogen), pSPORT1 (GIBCO BRL), pX (Pagano et al., *Science* 255: 1144-1147, 1992), yeast two-hybrid vectors such as pEG202 and dpJG4-5 (Gyuris et al., *Cell* 75: 791-803, 1995) or prokaryotic expression vectors such as lambda gt11 or pGEX (Amersham-Pharmacia). In addition to the nucleic acid molecules of the present invention, the vector can further comprise a polynucleotide encoding a secretion signal. The secretion signals are well known to those skilled in the art. And, depending on the expression system used, a leader sequence capable of guiding the translated protein to the cell compartment such as nuclei is combined with the coding sequence of the polynucleotide according to an embodiment of the present invention. Particularly, Klf4 is a kind of transcription factor belonging to the zinc finger protein. Thus, in order to enhance the translocation of Klf4 to the nucleus, a nuclear translocation promoting sequence or a nuclear localizing signal (NLS) derived from another proteins can be additionally introduced. Such an NLS can be one among NLS of SV-40 large T antigen (Chen et al., *J. Nucl. Med.* 47(5): 827-836, 2006), NLS of myopodin (Ganck et al., *FEBS Lett.*, 579(29): 6673-6680), NLS of nucleoplasmin (Dingwall and Laskey, *Trends Biochem. Sci.,* 16: 478-481, 1991), NLS of SRY (Sudbeck and Scherer, *J. Biol. Chem.* 272: 27848-27852, 1997), NLS of hnRNP A1 (Lee et al., *Cell,* 126: 543-558, 2006), NLS of Hrp1 (Lange et al., *J. Biol. Chem.* 283: 12926-12934, 2008), NLS of Borna disease Virus p10 (Wolff et al., *J. Biol. Chem.,* 277: 12515-12157, 2002), NLS of PLSCR1 (Chen et al., *J. Biol. Chem.* 280: 10599-10606, 2005), NLS of Ty1 Integrase (Moore et al., *Mol. Cell Biol.,* 18: 1105-1114, 1998), NLS of HIV-1 Rev (Cochrane et al., *J. Virol.,* 64: 881-885, 1990), NLS of HIV-1 Tat (Truant and Cullen, *Mol. Cell Biol.,* 19: 1210-1217, 1999), NLS of HTLV-1 Rex (Truant and Cullen, *Mol. Cell Biol.,* 19: 1210-1217, 1999), NLS of Ste12 (Leslie et al., *Mol. Cell Biol.,* 22: 2544-2555, 2002), NLS of Pho4 (Kafmann et al., *Genes Dev.,* 12: 2673-2683, 1998), NLS of Yap1 (Isoyama et al., *J. Biol. Chem.,* 276: 21863-21869, 2001). The above-described NLS is exemplary, and other well-known NLSs can be used.

In addition, the expression vector used in the present invention can be prepared by, for example, standard recombinant DNA technology, and the standard recombinant DNA technology includes, for example, ligation of blunt and adhesive ends, and treating with restriction enzymes for providing appropriate ends, removal of a phosphate group by alkaline phosphatase treatment to prevent improper bond, and enzymatic ligation by T4 DNA ligase, and the like. The vector of the present invention can be prepared by recombination of a DNA encoding a signal peptide obtained by chemical synthesis or genetic recombination technology, or a DNA encoding Klf4 protein according to an embodiment of the present invention, into a vector containing an appropriate regulatory sequence. A vector including the regulatory sequence can be purchased or prepared commercially.

In addition, in the method, the gene construct can further include a polynucleotide encoding one or more immune-stimulating peptides. In this case, the immune-stimulating peptide is in a form linked to a separate regulatory sequence, that is, in a bicistron form. It is included in the expression vector or linked to one regulatory sequence, but an internal ribosome entry site (IRES) can be inserted between the polynucleotides encoding the two proteins, transcribed into a single mRNA, and then translated into each protein. The immune-stimulating peptide can be CD28, ICOS (inducible costimulator), CTLA4 (cytotoxic T lymphocyte associated protein 4), PD1 (programmed cell death protein 1), BTLA (B and T lymphocyte associated protein), DR3 (death receptor 3), 4-1BB, CD2, CD40, CD40L, CD30, CD27, signaling lymphocyte activation molecule (SLAM), 2B4 (CD244), NKG2D (natural-killer group 2, member D)/DAP12 (DNAX-activating protein 12), TIM1 (T-cell immunoglobulin and mucin domain containing protein 1), TIM2, TIM3, TIGIT, CD226, CD160, LAG3 (lymphocyte activation gene 3), B7-1, B7-H1, GITR (glucocorticoid-induced TNFR family related protein), Flt3 ligand (fms-like tyrosine kinase 3 ligand), flagellin, herpesvirus entry mediator (HVEM), or the cytoplasmic domain of OX40L [ligand for CD134 (OX40), CD252], or a linkage of two or more thereof.

In the method, the Klf4 inducer can be APTO-253 {2-(5-fluoro-2-methyl-1H-indol-3-yl)-1H-imidazo[4,5-f][1,10] phenanthroline}.

In the method, the CD8 T cells can be transduced with a polynucleotide encoding Klf4 protein and/or treated with the Klf4 inducer.

In another aspect of the present invention, there is provided a pharmaceutical composition for treating cancer comprising CD8 T cells whose overexpression of Klf4 protein is induced as an active ingredient.

In the composition, the CD8 T cells whose overexpression of Klf4 protein can be autologous CD8 T cells isolated from a subject in need of treatment or heterologous CD8 T cells isolated from other subject, but preferably autologous CD8 T cells. The CD8 T cells which Klf4 protein is overexpressed can be prepared by transducing the CD8 T cells with a polynucleotide encoding Klf4 protein and/or treating the CD8 T cells with a Klf4 inducer.

The description of the transducing procedure and the Klf4 inducer is the same as described above.

In another aspect of the present invention, there is provided a transduced CD8 T cell which is transformed to overexpress the Klf4 protein.

The transduced CD8 T cells can be prepared by transducing CD8 T cells isolated from a subject in need of treatment or a cell population comprising the same with an expression vector containing a polynucleotide encoding a Klf4 protein. The expression vector can be a viral vector or a non-viral vector, and the viral vector can be an adeno-associated virus (AAV) vector, an adenovirus vector, an alphavirus vector, a herpes simplex virus vector, a vaccinia virus vector, or a Sendai virus vector., a flavivirus vector, a radovirus vector, a retroviral vector, a herpesvirus vector, a poxvirus vector or a lentiviral vector, and the non-viral vector can be am mRNA, a DNA vector, nanoparticles, cationic polymer, exosome, extracellular vesicle, or a liposome, and the DNA vector can be a plasmid vector, a cosmid vector, a phagemid vector, or an artificial human chromosome. In the transduced CD8 T cell, the mRNA can be used alone or in combination with the non-viral vector other than the mRNA encoding the Klf4 protein.

In another aspect of the present invention, there is provided a transduced CAR-CD8 T cell transduced to coexpress a heterologous Klf4 protein and a chimeric antigen receptor (CAR).

In the transduced CAR-CD8 T cell, the CAR can be a fusion protein comprising a single chain-based antibody mimetic, a transmembrane domain, a costimulatory factor and a cytoplasmic signaling domain.

In the transduced CAR-CD8 T cell, the single chain-based antibody mimetic can bind to a cancer antigen or an antigen derived from a pathogen specifically.

In the transduced CAR-CD8 T cell, the cancer antigen can be EpCAM (epithelial cell adhesion molecule), Trop-2 (trophoblast cell surface antigen 2), CEACAM5 (CEA cell adhesion molecule 5), CEACAM6 (CEA cell adhesion molecule 6), carcinoembryonic antigen (CEA), prostate-specific antigen prostatic acid phosphatase (PAP), prostate-specific membrane antigen (PSMA), Her2/neu, MUC-1, BCR/ABL, alpha-fetoprotein (AFP), an antigen derived from Epstein-Barr virus such as LMP2a, an antigen derived from human hepatitis B virus (HBV), human hepatitis C virus, Proteinase 3, WT-1, G250, melanoma antigen gene (MAGE), B melanoma antigen (BAGE), G melanoma antigen, NY-ESO-1, tyrosinase, tyrosinase-related protein-1 (TRP-1), TRP-2, gp100, MART-1, Ig Idiotype, CDK4, caspase-8, β-catenin, BCR/ABL, human papilloma virus antigen (HPV E6/E7), HHV-8, 5T4, p53, CA-125, CA-72-4, CA-15-3, or CA-19-9.

In the transduced CAR-CD8 T cell, the antigen derived from a pathogen can be an antigen derived from a pathogenic microorganism, a virus or a parasite.

In the transduced CAR-CD8 T cell, the pathogenic microorganism can be a pathogenic bacterium or a pathogenic fungus.

In the transduced CAR-CD8 T cell, the pathogenic bacterium can be *Bordetella pertussis*, tetanus, diphtheria, *Helicobacter pylori, Pneumococcus* sp., *Mycobacterium tuberoculosis, Cholera* sp., *Staphylococcus* sp., *Shigella* sp., *Borrelia* sp. or *Salmonella* sp.

In the transduced CAR-CD8 T cell, the pathogenic fungus can be Candida sp., Trichophyton sp., Aspergillus sp., Fonsecaea sp., Epidermophyton sp., Piedraia sp., Malassezia sp., Pseudallescheria sp., Basidiobolus sp., Conidiobolus sp., Rhinosporidium sp., Paracoccidioides sp., Cryptococcus sp., Blastomyces sp., Sporothrix sp., Mucor sp., Absidia sp., Rhizopus sp., Pneumocystis sp., Wangiella sp., Phialophora sp., or Schizophyllum sp.

In the transduced CAR-CD8 T cell, the virus can be influenza virus, human papilloma virus (HPV), vesicular stomatitis virus, cytomegalovirus (CMV), hepatitis A virus (HAV), hepatitis B virus (HBV), hepatitis C virus (HCV), hepatitis D virus (HDV), hepatitis G virus (HGV), respiratory synctytial virus (RSV), herpes simplex virus (HSV), or human immunodeficiency virus (HIV).

In the transduced CAR-CD8 T cell, the single chain-based antibody mimetic can be scFv, sdAb(single domain antibody), $V_HH$, $V_{NAR}$, Affibody, Affilin, Affimer, Affitin, Alphabody, Anticalin, Avimer, DARPin, Fynomer, Kunitz domain peptide, monobody, nanoCLAMP, variable lymphocyte receptor (VLR) or repebody.

In the transduced CAR-CD8 T cell, the transmebtrane domain can be a transmembrane doamin derived from 4-1BB/CD137, activated NK cell receptor, immunoglobulin protein, B7-H3, BAFFR, BLAME(SLAMF8), BTLA, CD100(SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD3 zetta, CD30, CD4, CD40, CD49a, CD49D, CD49f, CD69, CD7, CD84, CD8, CD8 alpha, CD8 beta, CD96 (Tactile), CD11a, CD11b, CD11c, CD11d, CDS, CEACAM1, CRT AM, cytokine receptor, DAP-10, DNAM1(CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T-cell costimulatory (ICOS), integrin, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, a ligand binding to CD83, LIGHT, LTBR, Ly9 (CD229), lymphocyte function-associated antigen-1 (LFA-1; CD1-1/CD18), MHC type 1 molecule, NKG2C, NKG2D, NKp30, NKp44, NKp46, NKp80 (KLRF1), OX-40, PAG/Cbp, programmed cell death-1 (PD-1), PSGL1, SELPLG (CD162), signaling lymphocytic activating molecule (SLAM), SLAMF1 (CD150 or IPO-3), SLAMF4 (CD244; 2B4), SLAMF6 (NTB-A; Ly108), SLAMF7, SLP-76, TNF receptor protein, TNFR2, TNFSF14, toll ligand receptor, TRANCE/RANKL, VLA1, or VLA-6.

In the transduced CAR-CD8 T cell, the costimulatory domain can be a cytoplasmic domain or a conjugate of at least two or more among selected from the group consisting of CD28, ICOS (inducible costimulator), CTLA4 (cytotoxic T lymphocyte associated protein 4), PD1 (programmed cell death protein 1), BTLA(B and T lymphocyte associated protein), DR3(death receptor 3), 4-1BB, CD2, CD40, CD30, CD27, SLAM(signaling lymphocyte activation molecule), 2B4(CD244), NKG2D (natural-killer group 2, member D)/DAP12 (DNAX-activating protein 12), TIM1 (T-Cell immunoglobulin and mucin domain containing protein 1), TIM2, TIM3, TIGIT, CD226, CD160, LAG3 (lymphocyte activation gene 3), B7-1, B7-H1, GITR (glucocorticoid-induced TNFR family related protein), HVEM(herpesvirus entry mediator) and OX40L (CD252).

In the transduced CAR-CD8 T cell, the cytoplasmic signaling domain can be one or more cytoplasmic domains selected from the group consisting of CD3δ, CD28, CD27, OX40/CD134, 4-1BB/CD137, FcεRIγ, ICOS/CD278, IL-2Rβ/CD122, IL-2Rα/CD132, DAP10, DAP12, and CD40.

In another aspect of the present invention, there is provided a composition comprising transformed CD8 T cells transduced to overexpress Klf4 protein or a transformed CAR-CD8 T cells transduced to overexpress Klf4 protein and a chimeric antigen receptor (CAR).

The composition can be used to treat a disease requiring an innate immune response, and the disease requiring an innate immune response can be cancer, a bacterial infection, a fungal infection, a viral infection, or a parasitic infection.

The composition can further include a pharmaceutically acceptable adjuvant, excipient or diluent in addition to the carrier.

As used herein, the term "pharmaceutically acceptable" refers to that is physiologically acceptable and does not normally cause gastrointestinal disorders, allergic reactions such as dizziness or similar reactions when administered to humans. Examples of such carriers, excipients and diluents include lactose, dextrose, sucrose, sorbitol, mannitol, xylitol, erythritol, maltitol, starch, gum acacia, alginate, gelatin, calcium phosphate, calcium silicate, cellulose, methyl cellulose, polyvinylpyrrolidone, water, methylhydroxybenzoate, propylhydroxybenzoate, talc, magnesium stearate and mineral oil. In addition, fillers, anti-agglomeration agents, lubricants, wetting agents, fragrances, emulsifiers and preservatives can be further included.

In addition, the pharmaceutical composition according to an embodiment of the present invention can be formulated using methods known in the art to enable rapid, sustained or delayed release of the active ingredient when administered to a mammal. Formulations include powders, granules, tablets, emulsions, syrups, aerosols, soft or hard gelatin capsules, sterile injectable solutions, and sterile powder forms.

The composition according to an embodiment of the present invention can be administered by various routes and can be administered by general systemic administration or local administration, for example, subcutaneous injection, intrasynovial injection, intraperitoneal injection, intramuscular injection, or intravenous injection. However, it is not limited thereto.

The composition according to an embodiment of the present invention can be formulated in a suitable form together with a commonly used pharmaceutically acceptable carrier. Pharmaceutically acceptable carriers include, for example, carriers for parenteral administration such as water, suitable oils, saline, aqueous glucose and glycol, and can further include stabilizers and preservatives. Suitable stabilizers include antioxidants such as sodium bisulfite, sodium sulfite or ascorbic acid. Suitable preservatives include benzalkonium chloride, methyl- or propyl-paraben and chlorobutanol. In addition, the composition according to the present invention can contain a suspending agent, a solubilizing agent, a stabilizer, an isotonic agent, a preservative, an adsorption inhibitor, a surfactant, a diluent, an excipient, a pH adjuster, an analgesic agent, a buffer, and antioxidants and the like can be included as appropriate. Pharmaceutically acceptable carriers and agents suitable for the present invention, including those exemplified above, are described in detail in Remington's Pharmaceutical Sciences, 15$^{th}$ Edition, 1975, Mack Publishing Company, Easton, Pennsylvania 18042 (Chapter 87: Blaug, Seymour), a formulation generally known in all pharmaceutical chemistries.

In addition, the composition of the present invention is administered in a therapeutically effective amount.

As used herein, the term "therapeutically effective amount" means an amount sufficient to treat a disease with a reasonable benefit/risk ratio applicable to medical treatment, and effective dose level includes the subject type and severity, age, sex, drug activity, sensitivity to drugs, administration time, administration route and excretion rate, duration of treatment, factors including concomitant drugs, and other factors well known in the medical field. The pharmaceutical composition of the present invention can be administered at a dose of 0.1 mg/kg to 1 g/kg, and more preferably at a dose of 1 mg/kg to 500 mg/kg. Meanwhile, the dosage can be appropriately adjusted according to the patient's age, sex, and condition.

The pharmaceutical composition of the present invention can be administered orally or parenterally. Preferably, parenteral administration is performed by intravenous injection, subcutaneous injection, intracerebroventricular injection, intracerebrospinal fluid injection, intramuscular injection and intraperitoneal injection.

In another aspect of the present invention, there is provided a method of treating a subject suffering from cancer comprising: preparing cells selected from the group consisting of a) CD8 T cells isolated from the subject, b) a cell population comprising the CD8 T cells, and a CAR-CD8 T cell prepared by transducing the CD8 T cells with a gene encoding a CAR; inducing overexpression of Klf4 protein in the cells by transducing the cells with a polynucleotide encoding the Klf4 protein or treating the cells with a Klf4 inducer; and administrating the CD8 T cells, the cell population comprising the CD8 T cells, or the CAR-CD8 T cell whose overexpression of Klf4 protein is induced to the subject.

In another aspect of the present invention, there is provided a method of treating cancer in a subject comprising: preparing induced CD8 T cells overexpressing Klf4 protein or transduced CAR-CD8 T cells expressing Klf4 protein; and administrating the induced CD8 T cells or transduced CAR-CD8 T cells to the subject.

In another aspect of the present invention, there is provided a method of treating cancer in a subject comprising: inducing overexpression of Klf4 protein in the cells selected from the group consisting of a) CD8 T cells isolated from the subject, b) a cell population comprising the CD8 T cells, and a CAR-CD8 T cell prepared by transducing the CD8 T cells with a gene encoding a CAR; and administrating the cells whose overexpression of Klf4 protein induced to the subject.

In the method, the overexpression of Klf4 protein is performed by transducing the CD8 T cells, the cell population or the CAR-CD8 T cells with an expression vector comprising a polynucleotide encoding Klf4 protein and/or treating the CD8 T cells, the cell population or the CAR-CD8 T cells with a Klf4 inducer.

In the method, the Klf4 inducer can be APTO-253.

The term "therapeutically effective amount" as used herein refers to an amount sufficient to treat a disease at a reasonable benefit/risk ratio applicable to medical treatment, and the effective dose level will depend on the type of subject and severity of the symptom, age, sex, sensitivity to the drug, time of administration, route of administration, rate of excretion, duration of treatment, factors including co-administered drugs, and other factors well known in the medical field. The amount to be used is not particularly limited but can be 0.01 μg/kg/day to 10 mg/kg/day. The above-mentioned daily dose can be administered once a day or twice or three times a day at appropriate intervals, or intermittently administered at intervals of several days.

BEST MODE FOR THE INVENTION

Hereinafter, the present invention will be described in more detail by following examples and experimental examples. It will be apparent to those skilled in the art that the present invention is not limited to the disclosed examples, but can be embodied in many different forms and the examples are provided in order to complete the disclosure of the present invention and to fully convey the scope of the invention to those skilled in the art.

EXAMPLES

Conventional Procedures
Construction of Retrovirus for Klf4 Gene Transduction

Platinum E cell line (platE, CELL BIOLABS, USA) was cultivated with DMEM medium (WELGENE) supplemented with 10% FBS (Gibco, USA), antibiotics streptomycin & penicillin (100 U/ml, WELGENE), and blastomycin (10 μg/ml, Gibco), and puromycin (1 μg/ml, Gibco) with care not to overgrow in consideration of cell confluency in a 5% $CO_2$ cell incubator at 37° C. When the cell confluency reached about 90%, the medium was removed, and then 5 ml of PBS (Sigma) was added to wash and then removed, and this washing process was repeated once more. Then, 2-3 ml of trypsin-EDTA solution (WELGENE) was added dropwise, and incubated for 3 minutes in a cell incubator at 37° C. Thereafter, the separated cells with 10 ml of DMEM medium were well pipetted, transferred to a 15 ml tube, and centrifuged for 5 minutes at 4° C. at 1,500 rpm. The supernatant was removed, and the pellet was resuspended in DMEM medium (antibiotic-free medium) supplemented with only 10% FBS, and then cells were counted. $2.5 \times 10^6$ platE cells in a 60 mm culture dish were resuspended in 3 ml of antibiotic-free DMEM medium, uniformly seeded, and cultured in a 37° C. 5% $CO_2$ cell incubator for 6-8 hours. MigRI-Klf4 vector was prepared by inserting the CDS sequence (SEQ ID NO: 1) of the mouse klf4 gene into MigRI vector (Addgene, USA). At this time, cloning of the mouse klf4 gene was performed through PCR amplification using a primer set (SEQ ID NOs: 2 and 3) to which restriction enzymes (BglII and EcoRI) recognition sites for cloning into the MigRI vector were added. ACC sequence was inserted as a Kozak sequence between the recognition site and the initiation codon (ATG). Then, 312.5 µl of 2× HBS was dispensed into one 1.5 ml centrifuge tube, and 38.75 µl of 2 M $CaCl_2$ and 10 µg of DNA vector were added to the other centrifuge tube, and the remainder was distilled using tertiary distilled water. Then, the centrifuge tube in which 2×HBS is dispensed is vortexed at low intensity, and the solution in the centrifuge tube in which the DNA vector is dispensed is transferred to the centrifuge tube in which 2×HBS is dispensed in a dropwise manner using a pipette and incubated at room temperature for 30 minutes. Then, the mixed solution was added in a dropwise manner to a platE culture dish prepared by seeding separated platE cells using a pipette. Then, the cells were incubated for about 16 hours at 37° C. in a 5% $CO_2$ cell incubator. After culturing, the culture medium was removed, washed twice with warm PBS, and 3 ml of DMEM medium without antibiotics added per 60 mm culture dish was dispensed and the cells were cultivated for additional 48 hours in a 37° C. 5% $CO_2$ cell incubator. After the culture was completed, only the culture supernatant was transferred and filtered using a 0.45 µm filter (ADVANTEC). The filtered supernatant containing the virus was immediately used for the experiment or was rapidly frozen dusing liquid nitrogen and then stored in a deep freezer at a temperature of −80° C.

Isolation and Activation of naïve CD8 T Cells

Mice were sacrificed and spleens were removed. Then, the spleen in PBS was finely crushed, filtered through a mesh, transferred to a 15 ml centrifuge tube, and centrifuged for 5 minutes at 4° C. and 1,500 rpm. The supernatant was removed, and the pellet was resuspended in 1 ml of Ack lysis buffer and incubated at room temperature for 3 minutes. Then, 10 ml of PBS was added and centrifuged for 5 minutes at 4° C. and 1500 rpm. Fluorescently labeled anti-CD8 antibody and anti-CD44 antibody were mixed in PBS at a volume ratio of 100:1 to prepare an antibody mixture, centrifuged and added to the settled cell pellet, resuspended, and incubated at 4° C. for 30 minutes. Then, 10 ml of PBS was added, followed by centrifugation for 5 minutes at 4° C. and 1,500 rpm. After removing the supernatant, the pellet was resuspended in 1 ml of PBS, filtered through a cell strainer, and cell density was adjusted by adding an appropriate amount of PBS or RPMI medium (WELGENE). Then, $CD8^+CD44^{low}$ cells (naïve CD8 T cells) were isolated using a cell sorter (SH800, Sony Biotechnology, USA).

A 48-well plate (SPL Life Sciences) is coated with anti-CD3 antibody 1 hour 30 minutes to 2 hours before separation is complete. Specifically, PBS is added so that the concentration of anti-CD3 antibody (Biolegend) is 5 µg/ml. 150 µl of each well of a 48-well plate was dispensed. Thereafter, the antibody was coated by incubating for about 1 hour 30 minutes to 2 hours in a cell incubator at 37° C. The antibody mixture was removed from each well of the antibody-coated plate and washed with 150 µl of PBS, and the same washing process was repeated once more. After the separation was completed, the naïve CD8 T cells were centrifuged at 4° C. and 1,500 rpm for 5 minutes, the supernatant was removed, and the pellet was resuspended with RPMI medium supplemented with 10% FBS, streptomycin & penicillin (100 U/ml), 2-mercaptoethanol (Gibco). $1.5 \times 10^6$ cells were added per well of the prepared anti-CD3 antibody-coated plate. At this time, anti-CD28 antibody (2 µg/ml, BD Pharmigen) and mIL-2 (100 U/ml, R&D Systems) were additionally treated. Then, it was cultured for 18-24 hours in a 37° C. 5% $CO_2$ cell incubator.

Transduction of Klf4 Gene Using Retrovirus

The cells activated for 18 to 24 hours were transferred to a 15 ml centrifuge tube and centrifuged for 5 minutes at 25° C. at 1,500 rpm. Subsequently, Percoll solutions diluted to 30% and 60%, respectively, were prepared using 100% Percoll, RPMI medium, and PBS. The centrifuged pellet was resuspended in 4 ml of 30% Percoll solution, and then 3 ml of 60% Percoll solution was carefully placed on the bottom layer. Then, it was centrifuged for 20 minutes under the conditions of 25° C. 2,000 rpm. At this time, acceleration and deceleration were set to minimum. After centrifugation, 3 ml of the upper layer was removed and the cells located at the interface were transferred to a new 15 ml centrifuge tube. Then, 10 ml of PBS was added and washed, followed by centrifugation at 25° C. at 1,500 rpm for 5 minutes. After centrifugation, the pellet was washed once again with 10 ml of PBS, centrifuged for 5 minutes at 25° C. and 1,500 rpm, and the cell pellet was resuspended in RPMI medium, and then the cells were counted. Then, cells were seeded at $5 \times 10^5$ per well in 12-well uncoated plates (SPL Life Sciences).

After adding 1-2 ml of the retroviral supernatant (MigRI-Klf4 and MigRI) prepared above to each well, mIL-2 (100 U/ml) and polybrene (8 µg/ml, Sigma) were added. Then, the crevice was sealed with parafilm and centrifuged for 1 hour at 25° C. at 1800×g. In this case as well, acceleration and deceleration were set to minimum. After centrifugation, the parafilm was removed and incubated for 30 minutes in a 37° C. 5% $CO_2$ cell incubator. Thereafter, the cells were transferred to a 15 ml centrifuge tube, washed by adding 10 ml of RPMI medium, and centrifuged at 25° C. for 5 minutes at 1,500 rpm. After centrifugation, the cell pellet was resuspended in 10 ml of RPMI medium, washed once again, and centrifuged at 25° C. at 1,500 rpm for 5 minutes. After centrifugation, the cell pellet was resuspended in PBS and immediately injected into mice intravenously to perform immune cell transfer (adoptive cell transfer), or to use for cell experiments through additional culture.

Induction of Klf4 Overexpression Using APTO-253

In addition to transduction of the Klf4 gene using retrovirus, the present inventors predicted that the overexpression of the Klf4 gene endogenous in naïve CD8 T cells would be possible by regulating the upstream signaling pathway of the transcription factor Klf4. Therefore, the present inventors hypothesize that overexpression of Klf4 protein by treating naïve CD8 cells with APTO-253 (Cercek et al., Invest. New. Drug. 33(5): 1086-1092, 2015), which is known as a Klf4 expression inducer, would show an effect similar to transduction using a vector.

Accordingly, in the same manner as above, after separating naïve CD8 T cells, naïve CD8 T cells were seeded on a plate coated with anti-CD3 antibody and in the process of activation, anti-CD28 antibody (2 μg/ml) and mIL-2 (100 U/ml) was treated with 3 μM of APTO-253 (MedChemExpress, LLC). Then, it was cultured for 72 hours in a 37° C. 5% $CO_2$ cell incubator. After completion of the culture, the cells were transferred to a 15 ml centrifuge tube, and the volume was adjusted to 3 ml by adding RPMI medium. After that, 3 ml of Histopaque (Sigma) was carefully placed in the lower layer. Then, centrifugation was carried out for 30 minutes at 25° C. at 2,000 rpm, and at this time, acceleration and deceleration were set to a minimum. After centrifugation, the culture solution of the upper layer was removed, and the cells present at the interface were recovered, transferred to a 15 ml centrifuge tube, resuspended in 10 ml of PBS, and centrifuged for 5 minutes at 4° C. and 1,500 rpm. After centrifugation, the supernatant was removed, the cell pellet was washed once more with 10 mL of PBS and centrifuged for 5 minutes at 4° C. and 1,500 rpm. After centrifugation, the supernatant was removed, the cell pellet was resuspended in an appropriate amount of PBS, and the cells were counted. Finally, $5 \times 10^5$ cells were diluted in 200 μl of PBS and loaded into a 1 ml syringe, and then intravenously injected into mice for immune cell transplantation.

Example 1: Study on the Mechanism of Exhaustion of CD8 T Cells

As described above, when CD8 T cells are chronically exposed to cancer antigens, etc., exhaustion occurs, and thus exhausted CD8 T cells do not undergo normal secretion of active cytokines and cell division, and thus cannot perform a proper immune response and normal function do not recover even though time passes.

Accordingly, the present inventors performed an experiment to mimic the exhaustion situation in vitro in order to determine the cause of the phenomenon that CD8 T cells are activated and then become exhausted over time.

1-1: In Vitro Exhaustion Experiment

To this end, the present inventors specifically isolated CD8 T cells from OT-I transgenic mice having OVA (ovalbumin)-peptide-specific T cell receptor (TCR) and repeatedly treated the OVA peptide for 5 days. All experimental sets were treated with IL-15 (5 ng/ml) and IL-7 (5 ng/ml) to increase the viability of CD8 T cells. After treatment with OVA peptide (10 ng/ml) and washing the next day, stimulation was repeatedly applied for 5 days in such a way that cytokines and OVA peptide were treated with the same composition again (repeated stimulation treatment group). At this time, as a control group, only a cytokine-treated group without OVA peptide treatment and a single stimulation treatment group in which OVA peptide (10 ng/ml) was treated for 2 days and washed, and then only cytokine was treated for 3 days were added. In addition, a set treated with IL-21, which is known to help activate CD8 T cells, was also added (repetitive stimulation+IL-21 treated group) (FIG. 1A). After 5 days, live CD8 T cells were isolated using a cell sorter, RNA was extracted, reverse transcribed into cDNA, and the expression levels of various genes were confirmed by qRT-PCR. As a result, the expression of the Tox gene, a representative marker of exhaustion, was increased in the repeated stimulation treatment group that mimics the exhaustion state, but the expression of the Tox gene decreased in the repeated stimulation+IL-21 treatment group. When the expression pattern of Klf4 was determined in this situation, the expression of the Klf4 gene was increased in the repeated stimulation treatment group but it was confirmed that the expression of the Klf4 gene was significantly increased in the repeated stimulation+IL-21 treatment group (FIG. 1B), unlike to Tox gene. This shows that CD8 T cells respond to IL-21, an activator, resulting in higher expression of Klf4 gene, suggesting that Klf4 can be a factor related to the activation of CD8 T cells in a state of exhaustion.

1-2: In Vivo Exhaustion Experiment

In order to confirm whether the results in the cell experiment of Example 1-1 can be reproduced in animal experiments, the present inventors performed exhaustion mimicry in vivo using experimental animals.

Specifically, spleen and tumor tissues were excised on day 18 after inoculation of MC38 cancer cells ($3 \times 10^5$) into C57BL/6 mice. Meanwhile, the animal experiments were performed according to the regulations of the Animal Experiment Ethics Committee of Seoul National University. In the spleen, $CD44^{low}$ naïve CD8 T cells with low CD44 expression and $CD44^{high}$ effector CD8 T cells with high CD44 expression upon antigen stimulation were isolated using a cell sorter. In tumor tissues, based on information known from previous studies, $Ly108^+$ CD8 T cells known as chronic progenitor cells, $Ly108^-CD69^-Tim3^+$ CD8 T cells known as chronic effector cells, and finally $Ly108^-CD69^+$ $Tim3^+$CD8 T cells, known as terminal exhausted CD8 T cells, were isolated using a cell sorter (FIG. 1C). RNA of the separated cells of 5 groups was extracted, reverse transcribed into cDNA, and expression levels of various genes were confirmed through qRT-PCR.

Figure 1D:
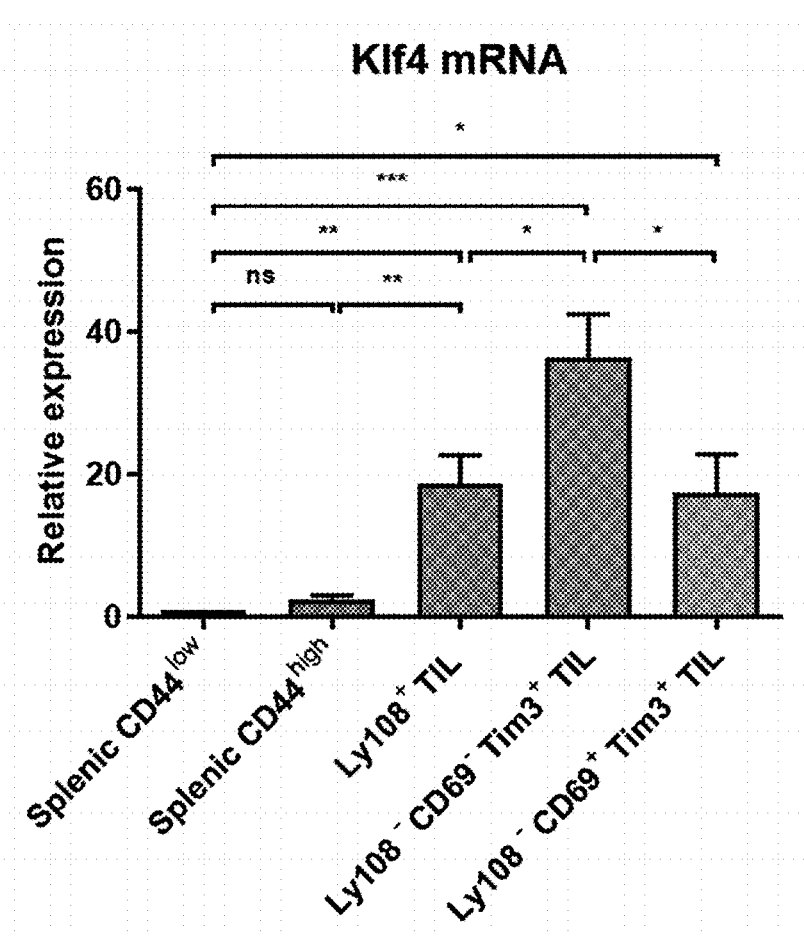
FIG. 1D is a graph showing the result of measuring expression level of Klf4 protein in the CD8 T cell subsets at the mRNA level.

As a result, in the case of Klf4, it was confirmed that the overall expression level in CD8 T cells in the exhausted state (chronic progenitor cells, chronic effector cells, and terminal exhausted cells) present in the tumor tissue was higher than that of the naïve CD8 T cells. In particular, it was confirmed that the expression of the Klf4 gene was highest in $Ly108^-$ $CD69^-Tim3^+$ CD8 T cells, known as chronic effector cells (FIG. 1D). From this, it was confirmed that CD8 T cells with high activity in the exhaustion state exhibited a higher Klf4 gene expression level in both in vitro and in vivo conditions.

Example 2: Preparation of Klf4 Overexpressing CD8 T Cells Through Gene Transduction From the results of Example 1 above, the present inventors hypothesized that Klf4 gene can promote generation and function of chronic effector cells based on the discovery that Klf4 expression was higher in the effector cells that maintain anticancer activity in the exhaustion state.

Accordingly, in order to confirm that the above hypothesis is true, the present inventors attempted to determine whether the generation of effector cells is promoted, and exhaustion caused by chronic stimulation to the antigen is suppressed and function of the effector cells is enhanced when the expression of Klf4 in CD8 T cells is artificially increased.

To this end, first, the present inventors transduced the isolated CD8 T cells with the Klf4 gene to perform an experiment for overexpressing the Klf4 gene.

Figure 2A:
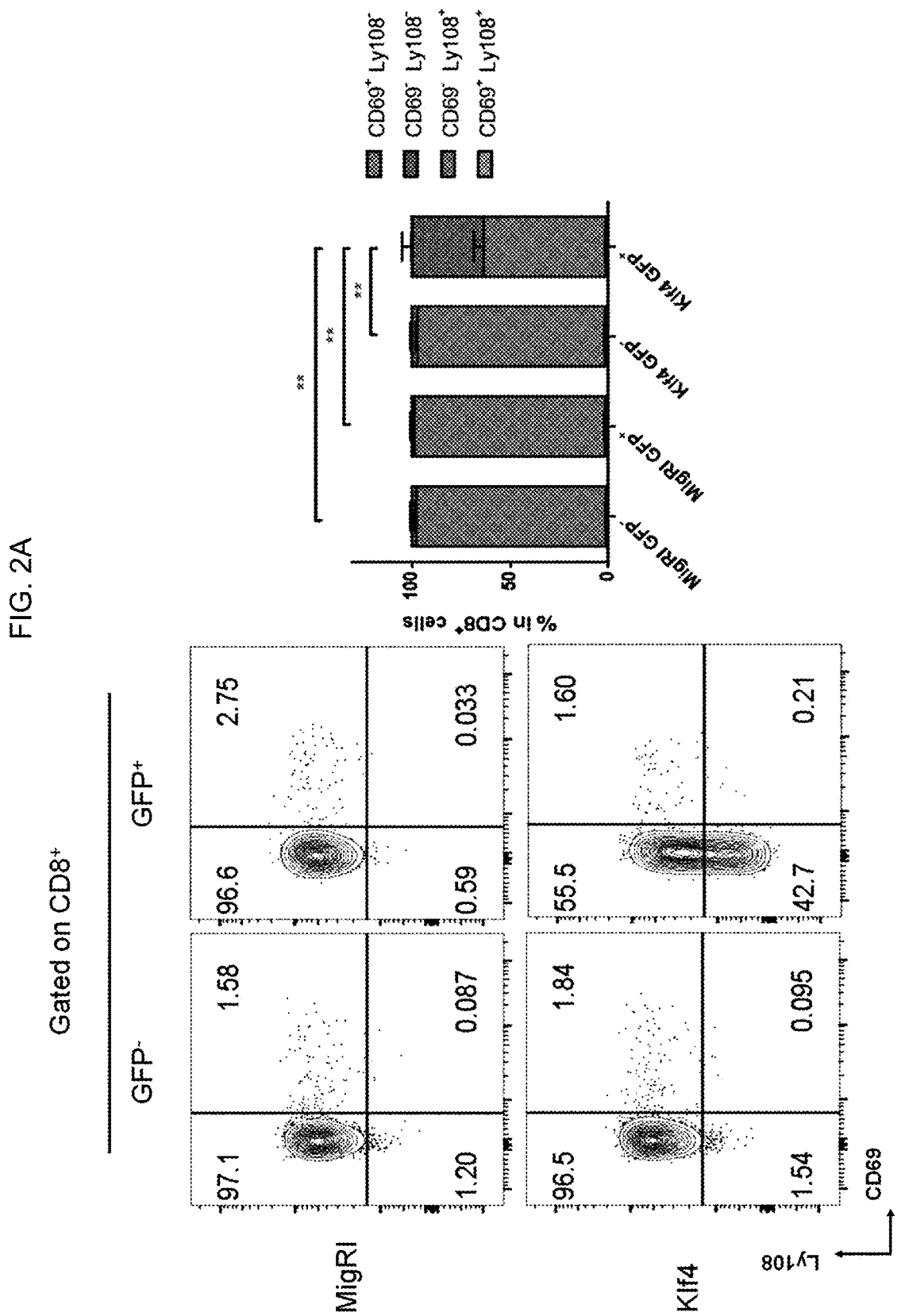
FIGS. 2A to 2E show the results of characterization of CD8 T cells transformed with a control retroviral vector (MigRI) or CD8 T cells transformed with a retroviral vector (Klf4) containing the Klf4 gene, according to an embodiment of the present invention.

Specifically, after treating CD8 T cells with anti-CD3 antibody, anti-CD28 antibody, and mIL-2 for 24 hours, and then the CD8 T cells were transduced with a retrovirus MigRI vector (control), and a recombinant retroviral MigRI vector in which Klf4 gene is inserted (hereinafter referred to as 'Klf4') as an experimental group in order to overexpress Klf4 protein. Transduction using retrovirus was performed using the general method described above. Thereafter, CD8 T cells were rested by treatment with mIL-7 and mIL-15 for 3 days. Since the MigRI vector basically expresses GFP, the CD8 T cells transduced with MigRI vector were GFP$^+$, and FACS analysis was performed. In the case of Klf4 GFP$^+$ CD8 T cells, the proportion of the aforementioned chronic effector cell (Ly108$^-$CD69$^-$) subset was significantly higher than that of the non-transduced control group, MigRI GFP$^-$, MigRI GFP$^+$, and Klf4 GFP$^-$, in which Klf4 was not overexpressed (FIG. 2A). This suggests that overexpression of Klf4 is an important factor in the development of chronic effector cell subsets.

Figure 2B:
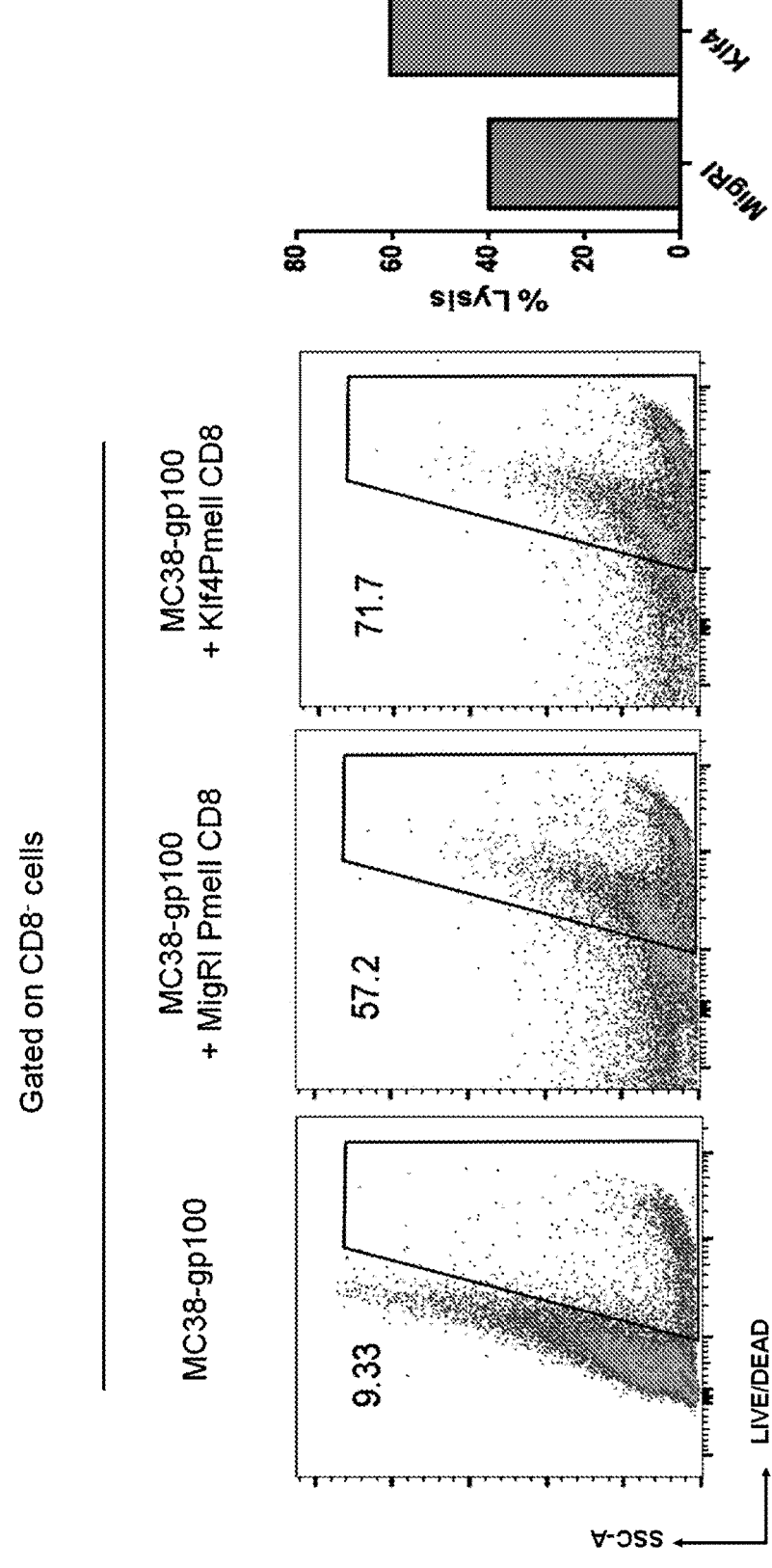

Next, to determine whether Klf4 overexpression promotes the function of effector cells, CD8 T cells derived from PmelI mice having a T cell receptor that specifically recognizes the gp100 antigen were isolated and transduced with control retroviral vector (MigRI) and recombinant retroviral vector (Klf4) by the above-described method. After the gene was overexpressed, the target cancer cells overexpressing the gp100 antigen (MC38-gp100) were co-cultured for 6 hours to measure the ratio of dead target cancer cells. As a result, compared to the control group (MigRI), when cultured with Pmell mice-derived CD8 T cells overexpressing the Klf4 gene, the ratio of dead target cancer cells increased, indicating that Klf4 overexpressing CD8 T cells could more effectively kill cancer cells (FIG. 2B).

Figure 2C:
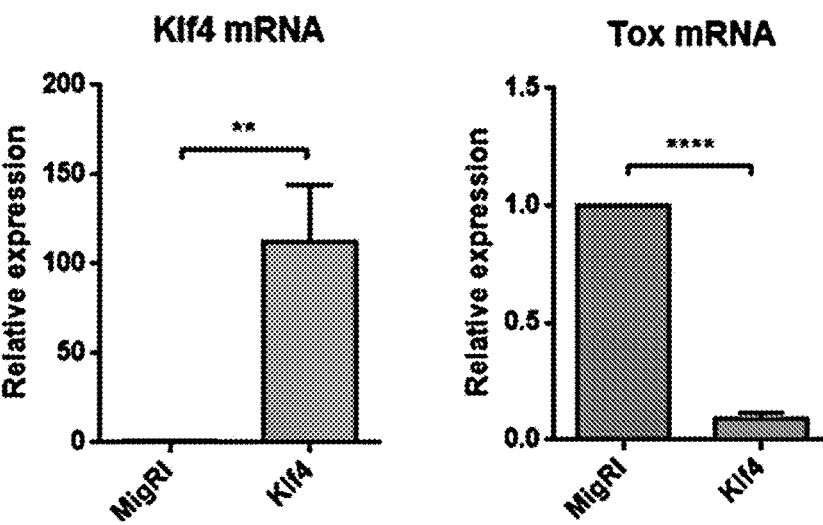
Figure 2D:
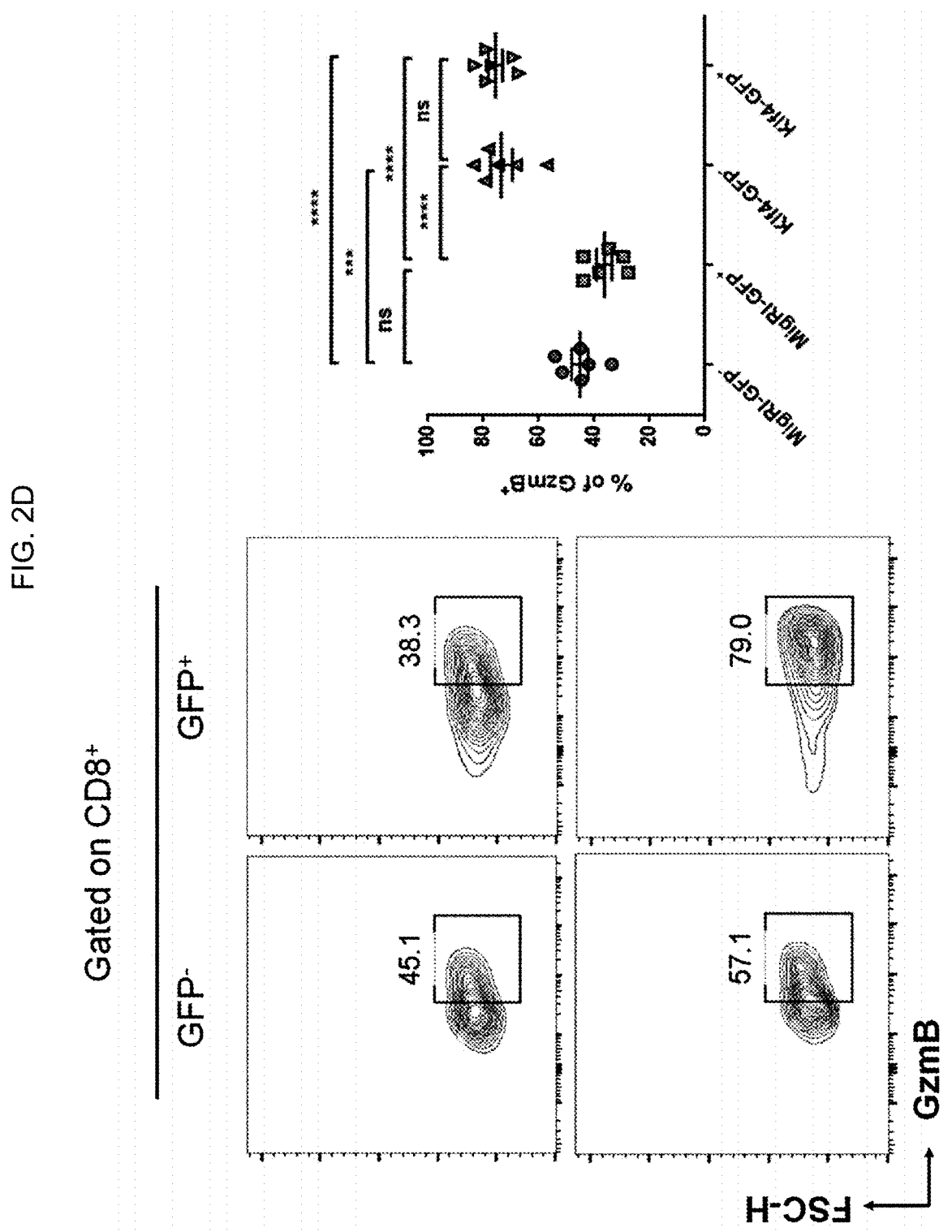
Figure 2E:
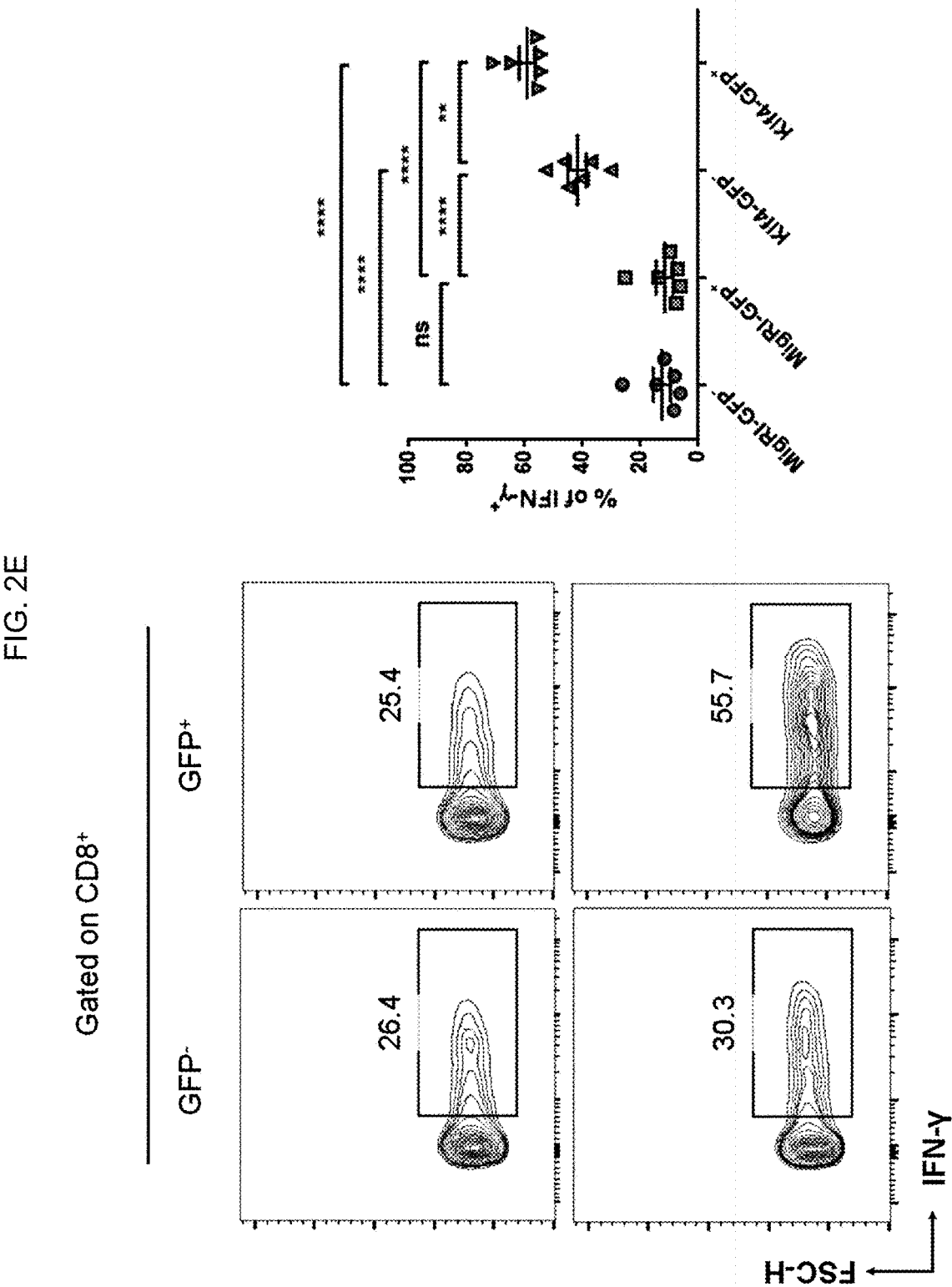

In addition, the in vitro exhaustion model performed in Example 1-1 was applied to confirm whether Klf4 overexpression promotes the function of chronic effector cells in the state of direct exhaustion. After 24 hours of treatment with OVA peptide, CD8 T cells were transduced with control retroviral vector (MigRI) and recombinant retroviral vector (Klf4), using retrovirus. After that, the OVA peptide was repeatedly treated for the remaining 4 days to induce in vitro exhaustion, and MigRI GFP$^+$ and Klf4 GFP$^+$ CD8 T cells were isolated using a cell sorter, and then gene expression was evaluated by qRT-PCR using the primer pairs shown in Table 1. As a result, Klf4 overexpressing CD8 T cells confirmed that Klf4 gene expression was much higher than that transduced with the control vector (MigRI), and at the same time, it was confirmed that the expression of the Tox gene, a marker of exhaustion, was significantly reduced (FIG. 2c). In addition, the amounts of granzyme B and interferon-gamma (IFN-γ) secreted from these CD8 T cells were measured through FACS analysis, and cytokine secretion was significantly increased in Klf4-overexpressed CD8 T cells (FIGS. 2D and 2E). From this result, it was confirmed that higher expression level of Klf4 gene promotes the formation of chronic effector cells (Ly108$^-$CD69$^-$) and the ability to kill target cancer cells, and suppresses further exhaustion in CD8 T cells in the exhaustion state as well as promotes secretion of more active cytokines.

TABLE 1

Primers used for qRT-PCR

| Gene | Primers | Sequences (5' -> 3') | SEQ ID NO: |
|------|---------|---------------------|------------|
| klf4 | forward primer | GTGCCCCGACTAACCGTTG | 7 |
|  | reverse primer | GTCGTTGAACTCCTCGGTCT | 8 |
| Tox | forward primer | CAACTCAAAGCCGTCAGTAT | 9 |
|  | reverse primer | GCTGAGGAGTCATTCCTGGT | 10 |

Figures 3A, 3B:
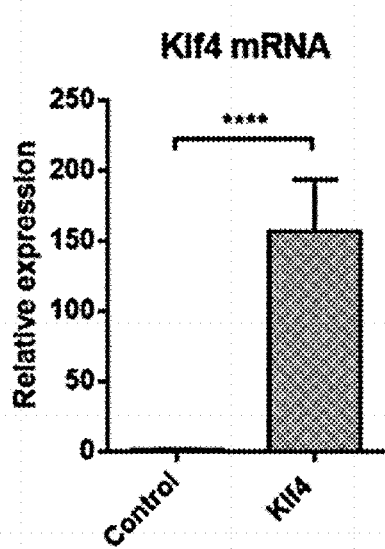
FIG. 3A is a schematic diagram schematically illustrating an administration schedule of an animal experiment using CD8 T cells transduced with Klf4 gene according to an embodiment of the present invention.
FIG. 3B is a graph showing the result of measuring the expression level of the Klf4 gene at the level of mRNA in the control group (Control) and CD8 T cells transduced with Klf4 gene (Klf4)
Figure 3C:
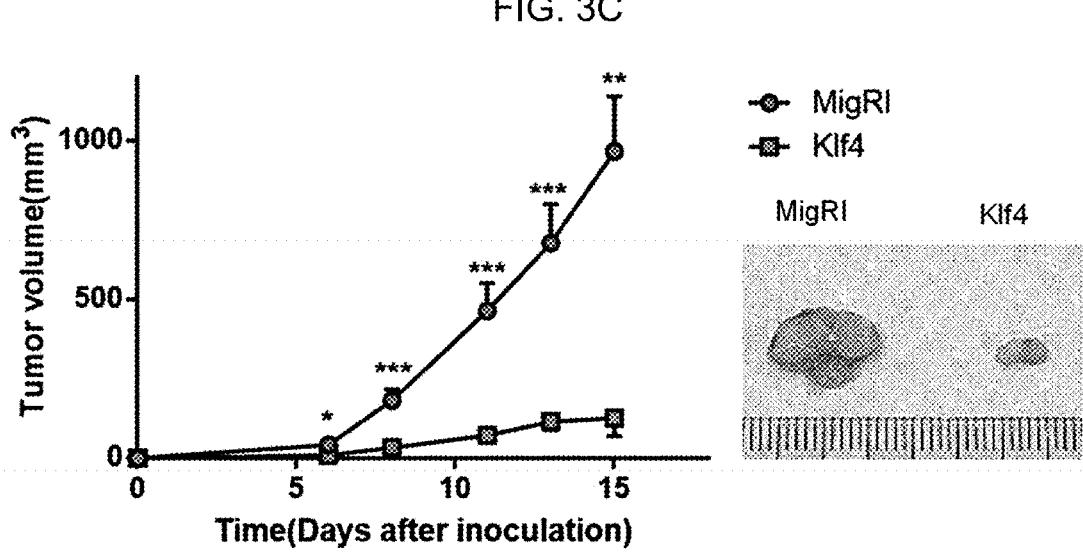
FIG. 3C shows a graph showing the change in the volume of the tumor tissue over time from excised from experimental animals administered with a control CD8 T cells (MigRI) or a CD8 T cell transformed with Klf4 gene (Klf4) according to an embodiment of the present invention, and a representative photograph of excised tumor tissues from the control group (MigRI) and experimental group (Klf4)
Figure 3D:
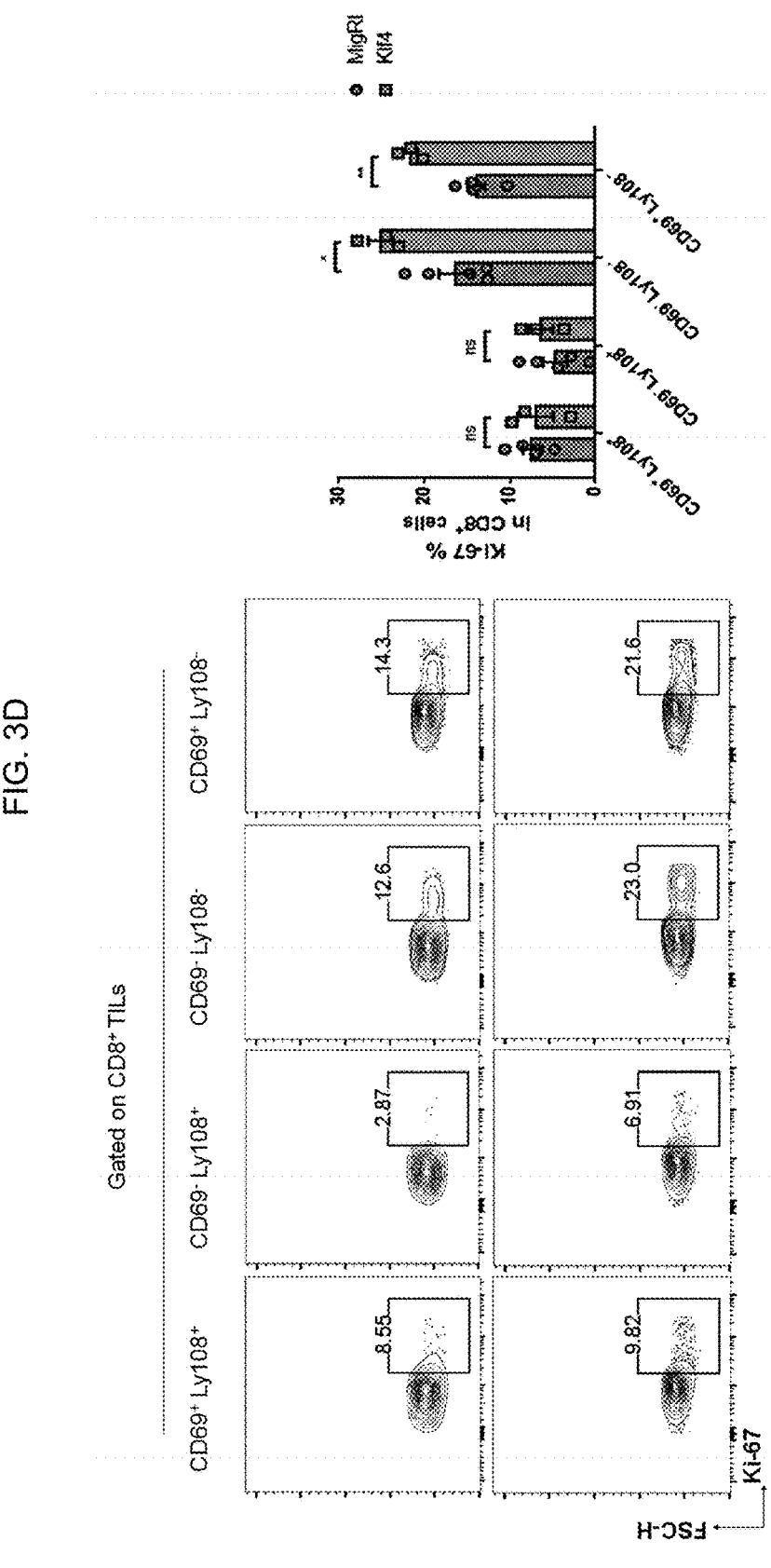
FIG. 3D shows a series of FACS histograms representing the proportion of CD8 T cells expressing Ki-67 indicating the degree of cell division in the various CD8 T cell subsets isolated from the tumor tissues of the animals sacrificed after the animal experiment (left), and a graph quantifying the FACS results (right)
Figure 3E:
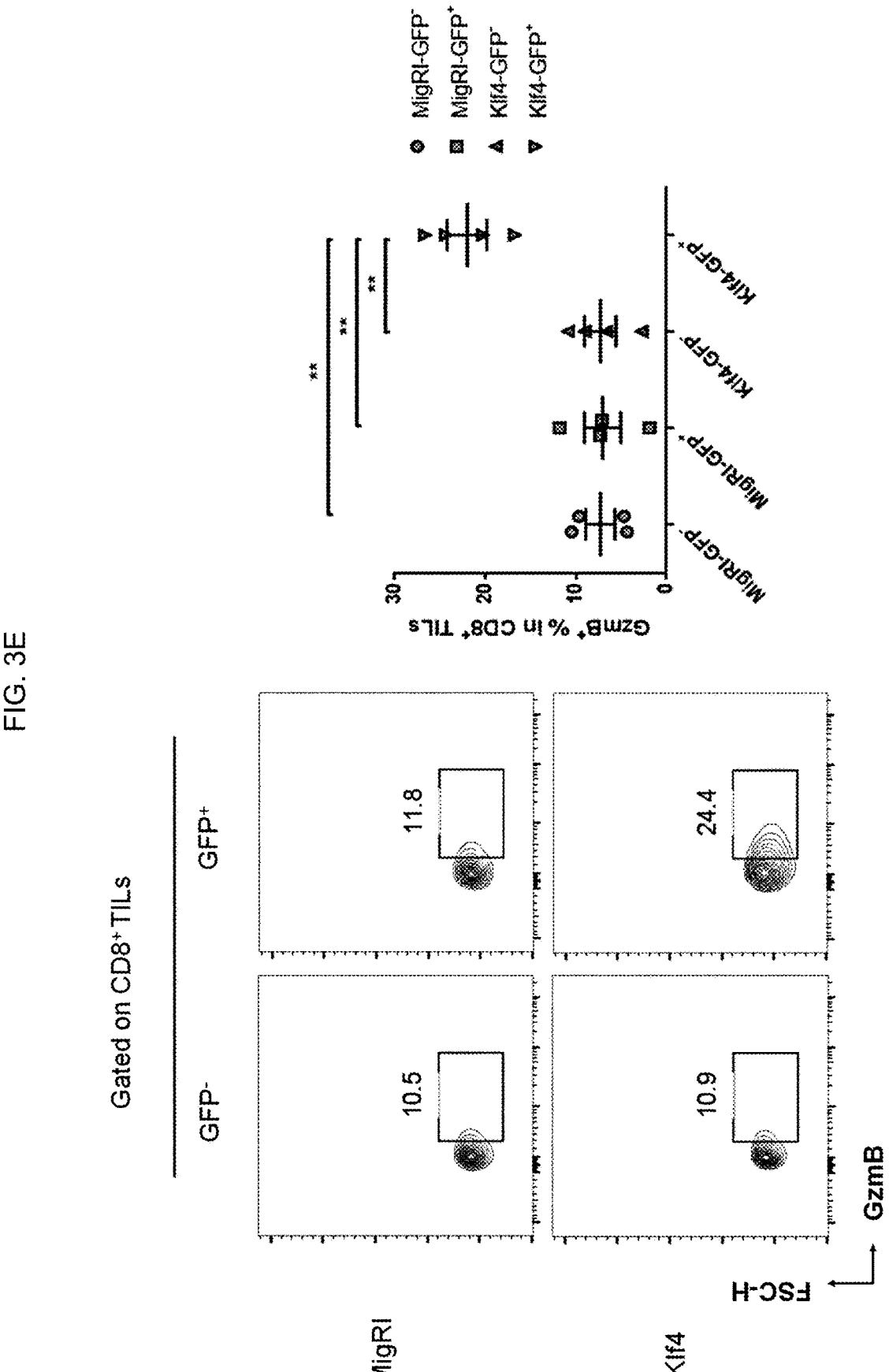
FIG. 3E shows a series of two-dimensional FACS histograms showing the results of measuring the ratio of granzyme B-expressing cells among CD8 T cells isolated from tumor tissues of animals sacrificed after the animal experiment (left) and a graph quantifying the FACS results (right)
Figure 3F:
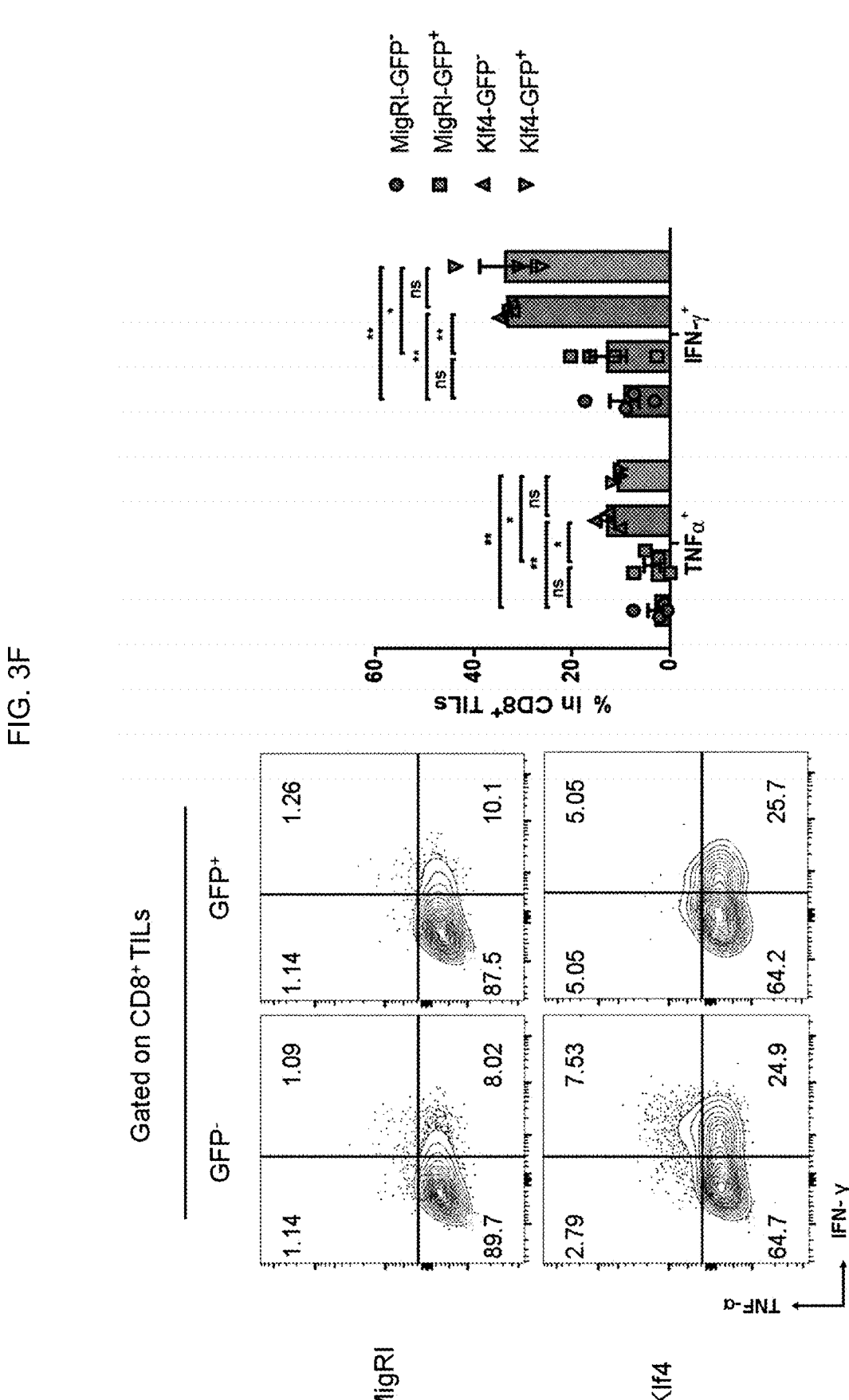
FIG. 3F represents a series of histograms showing the results of analyzing the expression levels of TNF-α and INF-γ in CD8 T cells isolated from tumor tissues of animals sacrificed after the animal experiment by FACS analysis (left) and a graph quantifying the FACS results (right).

Example 3: Analysis of Suppression of Exhaustion State Through Animal Experiments 3-1: Animal Experiment Through Klf4 Gene Transduction From the above results, the present inventors used a mouse tumor model to determine whether overexpression of Klf4 in CD8 T cells could inhibit cancer development by increasing cell activity even in vivo. Specifically, $3\times10^5$ gp100-expressing MC38 cancer cells (MC38-gp100) were inoculated into Rag2 KO mice, and a day later, and then CD8 T cells isolated from PmelI transgenic mice transduced which express gp100-specific TCR (Jackson Laboratory, received from the National Cancer Center) were transduced with the above-mentioned expression vector (MigRI and Klf4). $1\times10^6$ transduced CD8 T cells were administered to the tumor model mice through intravenous injection. The tumor volume was checked until the 15$^{th}$ day after inoculation of cancer cells, and mice were sacrificed at the end of the experiment and used for various analyses (FIG. 3A). Prior to transfer of transduced CD8 T cells into the mice, the expression level of Klf4 gene was confirmed. As a result, it was confirmed that the Klf4 gene was successfully overexpressed in the experimental group (FIG. 3B). In addition, it was confirmed that mice administered with CD8 T cells whose overexpression of Klf4 protein was induced showed dramatically decreased tumor volume compared to control mice administered with CD8 T cells transduced with MigRI (FIG. 3C). Further, FACS analysis shows that the expression level of Ki-67, as a measure of cell division, in the invasive CD8 T cell subsets present in the tumor tissue was significantly higher in CD8 T cells transduced with Klf4 compared to the control (MigRI) (FIG. 3D). As well, it was confirmed that all of the active cytokines such as granzyme B, IFN-γ, TNF-α were increased (FIGS. 3E and 3F). From these results, it was confirmed that the CD8 T cells transduced with Klf4 gene showed much better anticancer immune response than the control group.

3-2: Analysis of Suppression of Exhaustion State Using Klf4 Inducers

Figures 4A, 4B:
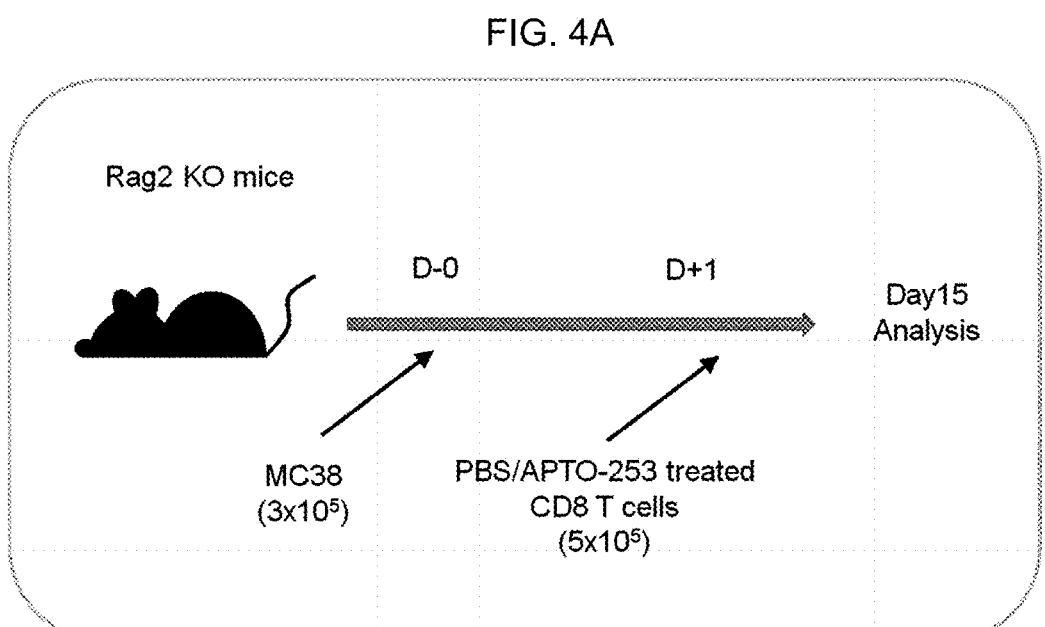
FIG. 4A is a schematic diagram schematically showing the administration schedule of an animal experiment using CD8 T cells treated with APTO-253 according to an embodiment of the present invention.
FIG. 4B is a graph showing the results of measuring the expression level of the Klf4 gene at the mRNA level in the experimental animals administrated with CD8 T cells treated with PBS (control) or APTO-253.
Figures 4C, 5:
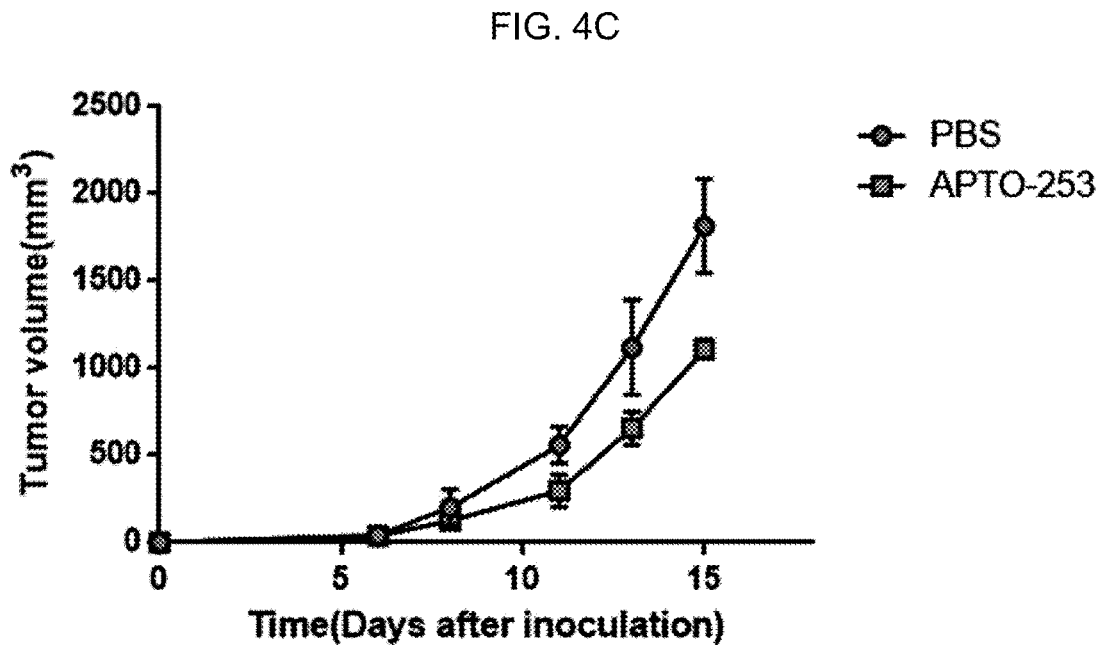
FIG. 4C is a graph showing the change in the volume of the tumor tissues excised from the experimental animals administered with CD8 T cells treated with PBS (control) or APTO-253 over time.
FIG. 5 is a schematic diagram showing various CAR constructs (EpCAM CAR, Trop-2 CAR, CEACAM6 CAR and CEACAM5 CAR) for the present invention.

From the results of Example 3-1, the present inventors hypothesized that if a drug capable of inducing Klf4 gene expression is used instead of transduction of the Klf4 gene, the anticancer effect could be increased according to the above results. An animal experiment was performed using APTO-253, which is known as an inducer of Klf4. Specifically, $3\times10^5$ MC38 cancer cells were injected into Rag2 KO mice lacking lymphocytes, and the next day, $5\times10^5$ CD8 T cells treated with PBS or APTO-253 for 3 days were intravenously administered. The tumor volume was checked until the 15$^{th}$ day after inoculation of cancer cells, and mice were sacrificed at the end of the experiment and used for various analyses (FIG. 4A). As a result of checking the Klf4 gene expression level in CD8 T cells treated with APTO-253 for 3 days prior to transfer into the mice, CD8 T cells treated with APTO-253 showed increased Klf4 gene expression level compared to CD8 T cells treated with PBS (FIG. 4B). In addition, it was confirmed that mice administered with CD8 T cells treated with APTO-253 showed decreased tumor growth compared to the mice administered with PBS-treated CD8 T cells, being consistent with the results from the Klf4 overexpression experiment analysis (FIG. 4C). From these results, it was confirmed that, in addition to Klf4 gene transduction, the increase in Klf4 gene expression in CD8 T cells through the Klf4 inducer APTO-253 also enhances the anticancer immune response of CD8 T cells.

According to an embodiment of the present invention, it was proved that CD8 T cells overexpressing the Klf4 gene by gene transduction or drug treatment suppress the immune exhaustion effect induced by repeated antigen stimulation in the living body, thereby killing cancer cells effectively through an innate immune response.

Example 4: Preparation of CAR-CD8 T Cell Whose Expression is Induced 4-1: Construction of EpCAM-Binding CAR Construct A schematic diagram showing an exemplary third-generation CAR construct is provided in FIG. 5. The CAR construct is produced as follows. The nucleotide sequence for the cDNA encoding a fusion protein CAR, comprising the amino acid sequences of anti-EpCAM scFv (SEQ ID NO: 11), CD8α hinge (SEQ ID NO: 12), CD28 TM (SEQ ID NO: 13), CD28 ICD (SEQ ID NO: 14), and CD3δ ICD (SEQ ID NO: 15) linked in tandem (EpCAM-CD28-CD3δ, FIG. 5) is synthesized by standard techniques, PCR-amplified, and ligated into pCLPS (Parry et al., *J. Immunol.,* 171: 166-174, 2003), a third generation self-inactivating lentiviral vector based on pRRL-SIN-CMV-eGFP-WPRE (Dull et al., *J. Virol.* 72: 8463-8471, 1998), or pELNS (Carpenito et al., *Proc. Natl. Acad. Sci. USA* 106: 3360-3365, 2009), which differs from pCLPS by replacing CMV with EF-1+ as the promoter for transgene expression. The encoded CAR comprises an scFv for binding to EpCAM (SEQ ID NO: 11).

4-2: Construction of Anti-Trop-2 CAR Construct

The lentiviral vector for expressing the CAR comprising anti-Trop-2 scFv (SEQ ID NO: 16), CD8α hinge, CD28, and CD3δICD linked in tandem (anti-Trop-2-CD28-CD3δ, FIG. 5) is constructed as described above except that the nucleotide sequence encoding anti-EpCAM-scFv is replaced by that of anti-Trop-2 scFv.

4-3: Construction of Anti-CEACAM6 CAR Construct

The lentiviral vector for expressing the CAR comprising anti-CEACAM6 scFv (SEQ ID NO: 17), CD8α hinge, CD28 TM, and CD3δ ICD linked in tandem (anti-CEACM6-CD28-CD3δ, FIG. 5) is constructed as described above except that the nucleotide sequence encoding anti-EpCAM is replaced by that of anti-CEACAM6 scFv.

4-4: Construction Anti-CEACAM5 CAR Construct

The lentiviral vector for expressing the CAR comprising anti-CEACAM5 scFv (SEQ ID NO: 18), CD8α hinge, CD28 TM, and CD3δ ICD linked in tandem (anti-CEACAM5-CD28-CD3δ, FIG. 5) is constructed as described above except that the nucleotide sequence encoding anti-EpCAM scFv is replaced by that of anti-CEACAM5 scFv.

Example 5: Production of Lentiviral Particles Including CAR Constructs

High-titer, replication-defective lentiviral vectors constructed as described in the Examples above are produced and concentrated as described by Parry et al. (*J. Immunol.,* 171: 166-174, 2003). Briefly, HEK 293T cells (ATCC CRL-3216) are cultured in RPMI 1640, 10% heat-inactivated FCS, 2 mM glutamine, 100 U/mL penicillin, and 100 μg/mL streptomycin sulfate. Cells are seeded at 5×106 per T 150 tissue culture flask 24 h before transfection with 7 μg of pMDG.1 (VSV-G envelop), 18 μg of pRSVrev (HIV-1 Rev encoding plasmid), 18 μg of pMDLg/p.RRE (packaging plasmid), and 15 μtg of the lentiviral vector of interest using Fugene 6 (Roche Molecular Biochemicals). Media are changed 6 h after transfection and the viral supernatant is harvested at 24 and 48 h posttransfection. Viral particles are concentrated 10-fold by ultracentrifugation for 3 h at 28,000 rpm with a Beckman SW28 rotor.

Example 6: Transduction of T Cells with CAR Lentiviruses

For certain purposes, T cells from normal individuals can be used with the subject CAR constructs for construct testing and design. Primary human CD4+ and CD8+ T cells are isolated from the PBMCs of healthy volunteer donors following leukapheresis by negative selection with RosetteSep kits (Stem Cell Technologies). T cells are cultured in complete media (RPMI 1640 supplemented with 10% heat-inactivated FCS, 2 mM glutamine, 100 U/mL penicillin, 100 μg/mL streptomycin sulfate, and 10 mM HEPES), stimulated with monoclonal anti-CD3 and anti-CD28 coated beads for 12 to 24 h, and transduced with a lentiviral vector of interest at MOI (multiplicity of infection) of 5 to 10. Human recombinant IL-2 is added every other day to a 50 U/mL final concentration and a cell density of 0.5 to $1.0 \times 10^6$ cells/mL is maintained. The Klf4 construct can be incorporated into the CAR construct or the transduction of the Klf4 construct can be performed simultaneously with the transduction of a separate CAR construct or can be performed sequentially.

Example 7: Generation and Assessment of Autologous CAR-T Cells From Cancer Patients The method as described by Brentjens et al. (*Sci. Transl. Med.* 5: 177ra38, 2013) is followed. Briefly, PBMCs are obtained from cancer patients by leukapheresis, washed, and cryopreserved. T cells are isolated from thawed leukapheresis product, activated with Dynabeads Human T-Activator CD3/CD28 magnetic beads (Invitrogen), and transduced with a lentiviral vector of interest. Transduced T cells are further expanded with the WAVE bioreactor to achieve the desired modified T cell dose.

Modified T cells are assessed for persistence in patient peripheral blood and bone marrow by FACS, anti-tumor activity by in vitro killing of antigen-positive cancer cells, and cytokine profiles by analyzing serial serum samples obtained before and after infusion of modified T cells with the Luminex IS 100 System and commercially available 39-plex cytokine detection assays (Brentjens, R. L. et al., *Blood* 118: 4817-4823, 2011).

While the present invention has been described with reference examples and experimental examples, it is to be understood that the invention is not limited to the disclosed exemplary examples, and on skilled in the art can comprehend that there are various modifications and equivalent examples. Accordingly, the true scope of the present invention should be determined by the technical idea of the appended claims.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be herein incorporated by reference.

What is claimed is:

1. An in vitro method of suppressing the exhaustion state of CD8 T cells comprising inducing overexpression of Klf4 protein in CD8 T cell-containing cells selected from the group consisting of a) CD8 T cells, b) a cell population comprising the CD8 T cells, and c) transduced CAR-CD8 T cells prepared by transducing the CD8 T cells with a gene encoding a chimeric antigen receptor (CAR), wherein the overexpression of the Klf4 protein is performed by transfecting the CD8 T cell-containing cells with an expression vector containing a polynucleotide encoding the Klf4 protein, or introducing an mRNA expressing the Klf4 protein into the CD8 T cell-containing cells.

2. The method according to claim 1, wherein the CD8 T cells are autologous cells isolated from a subject in need of treatment or heterologous cells isolated from other subject.

3. The method according to claim 1, wherein the expression vector is a viral vector or a non-viral vector.

4. The method according to claim 3, wherein the viral vector is an adeno-associated virus (AAV) vector, an adenovirus vector, an alphavirus vector, a herpes simplex virus vector, or a vaccinia virus vector, Sendaivirus vector, flavivirus vector, radovirus vector, retroviral vector, herpesvirus vector, poxvirus vector or lentiviral vector.

5. The method according to claim 3, wherein the non-viral vector is mRNA, a DNA vector, nanoparticles, cationic polymer, exosome, extracellular vesicle or liposome.

6. The method according to claim 5, wherein the DNA vector is a plasmid vector, a cosmid vector, a phagemid vector, or an artificial human chromosome.

7. The method according to claim 5, wherein the mRNA comprises a polynucleotide encoding a Klf4 protein, and the mRNA is used alone or in combination with a non-viral vector other than the mRNA.

8. The method according to claim 1, wherein the expression vector further comprises a polynucleotide encoding one or more immune-stimulating peptides.

9. The method according to claim 8, wherein the immune-stimulating peptide is CD28, ICOS (inducible costimulator), CTLA4 (cytotoxic T lymphocyte associated protein 4), PD1 (programmed cell death protein 1), BTLA (B and T lymphocyte associated protein), DR3 (death receptor 3), 4-1BB, CD2, CD40, CD40L, CD30, CD27, signaling lymphocyte activation molecule (SLAM), 2B4 (CD244), NKG2D (natural-killer group 2, member D)/DAP12 (DNAX-activating protein 12), TIM1 (T-cell immunoglobulin and mucin domain containing protein 1), TIM2, TIM3, TIGIT, CD226, CD160, LAG3 (lymphocyte activation gene 3), B7-1, B7-H1, GITR (glucocorticoid-induced TNFR family related protein), Flt3 ligand (fms-like tyrosine kinase 3 ligand), flagellin, herpesvirus entry mediator (HVEM), or the cytoplasmic domain of OX40L [ligand for CD134 (OX40), CD252], or a linkage of two or more thereof.

10. A pharmaceutical composition for treating cancer comprising CD8 T cells whose overexpression of Klf4 protein is induced as an effective ingredient, wherein the CD8 T cells whose overexpression of Klf4 protein is induced are prepared by transfecting the CD8 T cell with (a) an expression vector containing a polynucleotide encoding the Klf4 protein or (b) an mRNA expressing the Klf4 protein.

11. The pharmaceutical composition according to claim 10, wherein the CD8 T cells are autologous cells isolated from a subject in need of treatment or heterologous cells isolated from other subject.

12. A transduced CD8 T cell which is transformed to overexpress the Klf4 protein, wherein the transduced CD8 T cell is prepared by transfecting the CD8 T cell with (a) an expression vector containing a polynucleotide encoding the Klf4 protein or (b) an mRNA expressing the Klf4 protein.

13. The transduced CD8 T cell according to claim 12, wherein the expression vector is a viral vector or a non-viral vector.

14. The transduced CD8 T cell according to claim 13, wherein the viral vector is an adeno-associated virus (AAV) vector, an adenovirus vector, an alphavirus vector, a herpes simplex virus vector, a vaccinia virus vector, or a Sendai virus vector, a flavivirus vector, a radovirus vector, a retroviral vector, a herpesvirus vector, a poxvirus vector or a lentiviral vector.

15. The transduced CD8 T cell according to claim 13, wherein the non-viral vector is mRNA, a DNA vector, nanoparticles, cationic polymer, exosome, extracellular vesicle, or a liposome.

16. The transduced CD8 T cell according to claim 15, wherein the DNA vector is a plasmid vector, a cosmid vector, a phagemid vector, or an artificial human chromosome.

17. The transduced CD8 T cell according to claim 15, wherein the mRNA comprises a polynucleotide encoding a Klf4 protein, and the mRNA is used alone or in combination with a non-viral vector other than the mRNA.

18. A composition comprising the transduced CD8 T cell of claim 12.

19. A transduced CAR-CD8 T cell prepared by transducing a CD8 T cell isolated from a subject in need thereof or a cell population containing the CD8 T cell whose overexpression of Klf4 protein is induced with a gene encoding a chimeric antigen receptor (CAR), wherein the transduced CD8 T cell is prepared by transfecting the CD8 T cell with (a) an expression vector containing a polynucleotide encoding the Klf4 protein or (b) an mRNA expressing the Klf4 protein.

20. The transduced CAR-CD8 T cell according to claim 19, wherein the CAR is a fusion protein comprising a single chain-based antibody mimetic, a transmembrane domain, a costimulatory domain and a cytoplasmic signaling domain.

21. The transduced CAR-CD8 T cell according to claim 20, wherein the single chain-based antibody mimetic binds to a cancer antigen or an antigen derived from a pathogen specifically.

22. The transduced CAR-CD8 T cell according to claim 21, wherein the cancer antigen is EpCAM (epithelial cell adhesion molecule), Trop-2 (trophoblast cell surface antigen 2), CEACAM5 (CEA cell adhesion molecule 5), CEACAM6 (CEA cell adhesion molecule 6), carcinoembryonic antigen (CEA), prostate-specific antigen prostatic acid phosphatase (PAP), prostate-specific membrane antigen (PSMA), Her2/neu, MUC-1, BCR/ABL, alpha-fetoprotein (AFP), an antigen derived from Epstein-Barr virus such as LMP2a, an antigen derived from human hepatitis B virus (HBV), human hepatitis C virus, Proteinase 3, WT-1, G250, melanoma antigen gene (MAGE), B melanoma antigen (BAGE), G melanoma antigen, NY-ESO-1, tyrosinase, tyrosinase-related protein-1 (TRP-1), TRP-2, gp100, MART-1, Ig Idiotype, CDK4, caspase-8, β-catenin, BCR/ABL, human papilloma virus antigen (HPV E6/E7), HHV-8, 5T4, p53, CA-125, CA-72-4, CA-15-3, or CA-19-9.

23. The transduced CAR-CD8 T cell according to claim 21, wherein the antigen derived from a pathogen is an antigen derived from a pathogenic microorganism, a virus or a parasite.

24. The transduced CAR-CD8 T cell according to claim 23, wherein the pathogenic microorganism is a pathogenic bacterium or a pathogenic fungus.

25. The transduced CAR-CD8 T cell according to claim 24, wherein the pathogenic bacterium is *Bordetella pertussis*, tetanus, diphtheria, *Helicobacter pylori*, *Pneumococcus* sp., *Mycobacterium tuberoculosis, Cholera* sp., *Staphylococcus* sp., *Shigella* sp., *Borrelia* sp. or *Salmonella* sp.

26. The transduced CAR-CD8 T cell according to claim 24, wherein the pathogenic fungus is *Candida* sp., *Trichophyton* sp., *Aspergillus* sp., *Fonsecaea* sp., *Epidermophyton* sp., *Piedraia* sp., *Malassezia* sp., *Pseudallescheria* sp., *Basidiobolus* sp., *Conidiobolus* sp., *Rhinosporidium* sp., *Paracoccidioides* sp., *Cryptococcus* sp., *Blastomyces* sp., *Sporothrix* sp., *Mucor* sp., *Absidia* sp., *Rhizopus* sp., *Pneumocystis* sp., *Wangiella* sp., *Phialophora* sp., or *Schizophyllum* sp.

27. The transduced CAR-CD8 T cell according to claim 24, wherein the virus is influenza virus, human papilloma virus (HPV), vesicular stomatitis virus, cytomegalovirus (CMV), hepatitis A virus (HAV), hepatitis B virus (HBV), hepatitis C virus (HCV), hepatitis D virus (HDV) hepatitis G virus (HGV), respiratory synctytial virus (RSV), herpes simplex virus (HSV), or human immunodeficiency virus (HIV).

28. The transduced CAR-CD8 T cell according to claim 20, wherein the single chain-based antibody mimetic is scFv, sdAb (single domain antibody), VHH, VNAR, Affibody, Affilin, Affimer, Affitin, Alphabody, Anticalin, Avimer, DARPin, Fynomer, Kunitz domain peptide, monobody, nanoCLAMP, variable lymphocyte receptor (VLR) or repebody.

29. The transduced CAR-CD8 T cell according to claim 20, wherein the transmembrane domain is a transmembrane domain derived from 4-1BB/CD137, activated NK cell receptor, immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD3 zetta, CD30, CD4, CD40, CD49a, CD49D, CD49f, CD69, CD7, CD84, CD8, CD8 alpha, CD8 beta, CD96 (Tactile), CDlla, CDllb, CDllc, CDlld, CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T-cell costimulatory (ICOS), integrin, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, a ligand binding to CD83, LIGHT, LTBR, Ly9 (CD229), lymphocyte function-associated antigen-1 (LFA-1; CDI-la/CD18), MHC type 1 molecule, NKG2C, NKG2D, NKp30, NKp44, NKp46, NKp80 (KLRF1), OX-40, PAG/Cbp, programmed cell death-1 (PD-1), PSGL1, SELPLG (CD162), signaling lymphocytic activating molecule (SLAM), SLAMF1 (CD150 or IPO-3), SLAMF4 (CD244; 2B4), SLAMF6 (NTB-A; Ly108), SLAMF7, SLP-76, TNF receptor protein, TNFR2, TNFSF14, toll ligand receptor, TRANCE/RANKL, VLA1, or VLA-6.

30. The transduced CAR-CD8 T cell according to claim 20, the costimulatory domain is a cytoplasmic domain or a conjugate of at least two or more among selected from the group consisting of CD28, ICOS (inducible costimulator), CTLA4 (cytotoxic T lymphocyte associated protein 4), PD1 (programmed cell death protein 1), BTLA (B and T lymphocyte associated protein), DR3 (death receptor 3), 4-1BB, CD2, CD40, CD30, CD27, SLAM (signaling lymphocyte activation molecule), 2B4 (CD244), NKG2D (natural-killer group 2, member D)/DAP12 (DNAX-activating protein 12), TIM1 (T-Cell immunoglobulin and mucin domain containing protein 1), TIM2, TIM3, TIGIT, CD226, CD160, LAG3 (lymphocyte activation gene 3), B7-1, B7-H1, GITR (glucocorticoid-induced TNFR family related protein), HVEM (herpesvirus entry mediator) and OX40L (CD252).

31. The transduced CAR-CD8 T cell according to claim 20, wherein the cytoplasmic signaling domain is one or more cytoplasmic domains selected from the group consisting of CD35, CD28, CD27, OX40/CD134, 4-1BB/CD137, FcεRIγ, ICOS/CD278, IL-2Rβ/CD122, IL-2Rα/CD132, DAP10, DAP12, and CD40.

32. A composition comprising transformed CD8 T cells transduced to overexpress Klf4 protein, a cell population containing the transduced CD8 T cells, or a transduced CAR-CD8 T cells transduced to overexpress Klf4 protein and a chimeric antigen receptor (CAR).

33. The composition according to claim 32, wherein the composition is used for treating a disease requiring an innate immune response.

34. The composition according to claim 33, wherein the disease requiring an innate immune response is cancer, a bacterial infection, a fungal infection, a viral infection, or a parasitic infection.

35. A method of treating a subject suffering from cancer comprising: preparing CD8 T cell-cells selected from the group consisting of a) CD8 T cells isolated from the subject, b) a cell population comprising the CD8 T cells, and c) transduced CAR-CD8 T cells prepared by transducing the CD8 T cells with a gene encoding a CAR; inducing overexpression of Klf4 protein in the CD8 T cell-containing cells by transducing the CD8 T cell-containing cells with (a) an expression vector containing a polynucleotide encoding the Klf4 protein or (b) an mRNA expressing the Klf4 protein, or treating the CD8 T cell-containing cells with a Klf4 inducer; and administrating the CD8 T cell-containing cells whose expression of Klf4 protein is induced to the subject.

36. The method according to claim 35, wherein the Klf4 inducer is APTO-253.

37. The method according to claim 35, wherein the CD8 T cells are autologous cells isolated from the subject or heterologous cells isolated from other subject.

38. The method according to claim 37, wherein the CD8 T cell-containing cells whose overexpression of Klf4 protein is induced is prepared by inducing overexpression of Klf4 protein in the CD8 T cells, a cell population containing the CD8 T cells or transduced CAR-CD8 T cells transduced with a gene construct encoding the CAR by transducing the cells with a gene construct encoding Klf4 protein or treating the cells with a Klf4 inducer.

39. The method according to claim 38, wherein the Klf4 inducer is APTO-253.

40. An in vitro method of enhancing immune response of CD8 T cells comprising inducing overexpression of Klf4 protein in the cells, wherein the cells are selected from the group consisting of a) CD8 T cells isolated from a subject, b) a cell population comprising the CD8 T cells, and c) CAR-CD8 T cells prepared by transducing the CD8 T cells with a gene encoding a chimeric antigen receptor (CAR).

41. An in vitro method of proliferating CD8 T cells isolated from a subject comprising inducing overexpression of Klf4 protein in CD8 T cell-containing cells selected from the group consisting of a) CD8 T cells isolated from a subject, b) a cell population comprising the CD8 T cells, and c) CAR-CD8 T cells prepared by transducing the CD8 T cells with a gene encoding a chimeric antigen receptor (CAR).

42. A pharmaceutical composition for treating cancer comprising CD8 T cell-containing cells whose expression of Klf4 is induced, wherein the cells are selected from the group consisting of: a) CD8 T cells isolated from a subject, b) a cell population containing the CD8 T cells, and c) CAR-CD8 T cells prepared by transducing the CD8 T cell-containing cells with a gene construct encoding a chimeric antigen receptor as an active ingredient, wherein the CD8 T cell-containing cells whose expression of Klf4 is induced are prepared by transfecting the CD8 T cells or the CAR-CD8 T cells with (a) an expression vector containing a polynucleotide encoding the Klf4 protein or (b) an mRNA expressing the Klf4 protein.

\* \* \* \* \*

SEQUENCE LISTING

<160> NUMBER OF SEQ ID NOS: 18

<210> SEQ ID NO 1
<211> LENGTH: 1452
<212> TYPE: DNA
<213> ORGANISM: Mus msculus

<400> SEQUENCE: 1
atgaggcagc cacctggcga gtctgacatg gctgtcagcg acgctctgct cccgtccttc      60
tccacgttcg cgtccggccc ggcgggaagg gagaagacac tgcgtccagc aggtgccccg     120
actaaccgtt ggcgtgagga actctctcac atgaagcgac ttcccccact tcccggccgc     180
ccctacgacc tggcggcgac ggtggccaca gacctggaga gtggcggagc tggtgcagct     240
tgcagcagta acaacccggc cctcctagcc cggagggaga ccgaggagtt caacgacctc     300
ctggacctag actttatcct ttccaactcg ctaacccacc aggaatcggt ggccgccacc     360
gtgaccacct cggcgtcagc ttcatcctcg tcttccccgg cgagcagcgg ccctgccagc     420
gcgccctcca cctgcagctt cagctatccg atccgggccg ggggtgaccc gggcgtggct     480
gccagcaaca caggtggagg gctcctctac agccgagaat ctgcgccacc tcccacggcc     540
cccttcaacc tggcggacat caatgacgtg agccctcgg cggcttcgt ggctgagctc        600 ctgcggccgg agttggaccc agtatacatt ccgccacagc agcctcagcc gccaggtggc     660
gggctgatgg gcaagtttgt gctgaaggcg tctctgacca ccctggcag cgagtacagc       720 agcccttcgg tcatcagtgt tagcaaagga agcccagacg gcagccaccc cgtggtagtg     780
gcgccctaca gcggtggccc gccgcgcatg tgccccaaga ttaagcaaga ggcggtcccg     840
tcctgcacgg tcagccggtc cctagaggcc catttgagcg ctggacccca gctcagcaac     900
ggccaccggc ccaacacaca cgacttcccc ctggggcggc agctccccac caggactacc     960
cctacactga gtcccgagga actgctgaac agcagggact gtcaccctgg cctgcctctt    1020
cccccaggat tccatcccca tccggggccc aactaccctc ctttcctgcc agaccagatg    1080
cagtcacaag tccctctct ccattatcaa gagctcatgc caccgggttc ctgcctgcca     1140
gaggagccca agccaaagag gggaagaagg tcgtggcccc ggaaaagaac agccacccac    1200
acttgtgact atgcaggctg tggcaaaacc tataccaaga gttctcatct caaggcacac    1260
ctgcgaactc acacaggcga gaaaccttac cactgtgact gggacggctg tgggtggaaa    1320
ttcgcccgct ccgatgaact gaccaggcac taccgcaaac acacagggca ccggcccttt    1380
cagtgccaga gtgtgacag ggcctttcc aggtcggacc accttgcctt acacatgaag      1440
aggcactttt aa                                                         1452

<210> SEQ ID NO 2
<211> LENGTH: 29
<212> TYPE: DNA
<213> ORGANISM: Artificial Sequence
<220> FEATURE:
<223> OTHER INFORMATION: Forward primer coloning klf4 gene

<400> SEQUENCE: 2
agatctacca tgaggcagcc acctggcga                                          29

<210> SEQ ID NO 3
<211> LENGTH: 36
<212> TYPE: DNA
<213> ORGANISM: Artificial Sequence
<220> FEATURE:
<223> OTHER INFORMATION: Reverse primer for cloning klf4 gene

```
<400> SEQUENCE: 3
gaattcttaa aagtgcctct tcatgtgtaa ggcaag                                    36

<210> SEQ ID NO 4
<211> LENGTH: 483
<212> TYPE: PRT
<213> ORGANISM: Mus musulus

<400> SEQUENCE: 4

Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
            20                  25                  30

Thr Leu Arg Pro Ala Gly Ala Pro Thr Asn Arg Trp Arg Glu Glu Leu
        35                  40                  45

Ser His Met Lys Arg Leu Pro Pro Leu Pro Gly Arg Pro Tyr Asp Leu
    50                  55                  60

Ala Ala Thr Val Ala Thr Asp Leu Glu Ser Gly Gly Ala Gly Ala Ala
65                  70                  75                  80

Cys Ser Ser Asn Asn Pro Ala Leu Leu Ala Arg Arg Glu Thr Glu Glu
                85                  90                  95

Phe Asn Asp Leu Leu Asp Leu Asp Phe Ile Leu Ser Asn Ser Leu Thr
            100                 105                 110

His Gln Glu Ser Val Ala Ala Thr Val Thr Thr Ser Ala Ser Ala Ser
        115                 120                 125

Ser Ser Ser Ser Pro Ala Ser Ser Gly Pro Ala Ser Ala Pro Ser Thr
    130                 135                 140

Cys Ser Phe Ser Tyr Pro Ile Arg Ala Gly Gly Asp Pro Gly Val Ala
145                 150                 155                 160

Ala Ser Asn Thr Gly Gly Gly Leu Leu Tyr Ser Arg Glu Ser Ala Pro
                165                 170                 175

Pro Pro Thr Ala Pro Phe Asn Leu Ala Asp Ile Asn Asp Val Ser Pro
            180                 185                 190

Ser Gly Gly Phe Val Ala Glu Leu Leu Arg Pro Glu Leu Asp Pro Val
        195                 200                 205

Tyr Ile Pro Pro Gln Gln Pro Gln Pro Pro Gly Gly Gly Leu Met Gly
    210                 215                 220

Lys Phe Val Leu Lys Ala Ser Leu Thr Thr Pro Gly Ser Glu Tyr Ser
225                 230                 235                 240

Ser Pro Ser Val Ile Ser Val Ser Lys Gly Ser Pro Asp Gly Ser His
                245                 250                 255

Pro Val Val Val Ala Pro Tyr Ser Gly Gly Pro Pro Arg Met Cys Pro
            260                 265                 270

Lys Ile Lys Gln Glu Ala Val Pro Ser Cys Thr Val Ser Arg Ser Leu
        275                 280                 285

Glu Ala His Leu Ser Ala Gly Pro Gln Leu Ser Asn Gly His Arg Pro
    290                 295                 300

Asn Thr His Asp Phe Pro Leu Gly Arg Gln Leu Pro Thr Arg Thr Thr
305                 310                 315                 320

Pro Thr Leu Ser Pro Glu Glu Leu Leu Asn Ser Arg Asp Cys His Pro
                325                 330                 335

Gly Leu Pro Leu Pro Pro Gly Phe His Pro His Pro Gly Pro Asn Tyr
            340                 345                 350
```

-continued

```
Pro Pro Phe Leu Pro Asp Gln Met Gln Ser Gln Val Pro Ser Leu His
    355             360             365

Tyr Gln Glu Leu Met Pro Pro Gly Ser Cys Leu Pro Glu Glu Pro Lys
    370             375             380

Pro Lys Arg Gly Arg Arg Ser Trp Pro Arg Lys Arg Thr Ala Thr His
385             390             395             400

Thr Cys Asp Tyr Ala Gly Cys Gly Lys Thr Tyr Thr Lys Ser Ser His
            405             410             415

Leu Lys Ala His Leu Arg Thr His Thr Gly Glu Lys Pro Tyr His Cys
            420             425             430

Asp Trp Asp Gly Cys Gly Trp Lys Phe Ala Arg Ser Asp Glu Leu Thr
            435             440             445

Arg His Tyr Arg Lys His Thr Gly His Arg Pro Phe Gln Cys Gln Lys
    450             455             460

Cys Asp Arg Ala Phe Ser Arg Ser Asp His Leu Ala Leu His Met Lys
465             470             475             480

Arg His Phe
```

<210> SEQ ID NO 5
<211> LENGTH: 504
<212> TYPE: PRT
<213> ORGANISM: Homo sapiens

<400> SEQUENCE: 5

```
Met Ala Val Ser Asp Ala Leu Leu Pro Ser Phe Ser Thr Phe Ala Ser
1               5               10              15

Gly Pro Ala Gly Arg Glu Lys Thr Leu Arg Gln Ala Gly Ala Pro Asn
            20              25              30

Asn Arg Trp Arg Glu Glu Leu Ser His Met Lys Arg Leu Pro Pro Val
            35              40              45

Leu Pro Gly Arg Pro Tyr Asp Leu Ala Ala Ala Thr Val Ala Thr Asp
    50              55              60

Leu Glu Ser Gly Gly Ala Gly Ala Ala Cys Gly Gly Ser Asn Leu Ala
65              70              75              80

Pro Leu Pro Arg Arg Glu Thr Glu Glu Phe Asn Asp Leu Leu Asp Leu
                85              90              95

Asp Phe Ile Leu Ser Asn Ser Leu Thr His Pro Pro Glu Ser Val Ala
            100             105             110

Ala Thr Val Ser Ser Ser Ala Ser Ala Ser Ser Ser Ser Ser Pro Ser
            115             120             125

Ser Ser Gly Pro Ala Ser Ala Pro Ser Thr Cys Ser Phe Thr Tyr Pro
    130             135             140

Ile Arg Ala Gly Asn Asp Pro Gly Val Ala Pro Gly Gly Thr Gly Gly
145             150             155             160

Gly Leu Leu Tyr Gly Arg Glu Ser Ala Pro Pro Pro Thr Ala Pro Phe
            165             170             175

Asn Leu Ala Asp Ile Asn Asp Val Ser Pro Ser Gly Gly Phe Val Ala
            180             185             190

Glu Leu Leu Arg Pro Glu Leu Asp Pro Val Tyr Ile Pro Pro Gln Gln
            195             200             205

Pro Gln Pro Pro Gly Gly Gly Leu Met Gly Lys Phe Val Leu Lys Ala
    210             215             220

Ser Leu Ser Ala Pro Gly Ser Glu Tyr Gly Ser Pro Ser Val Ile Ser
225             230             235             240
```

```
Val Ser Lys Gly Ser Pro Asp Gly Ser His Pro Val Val Val Ala Pro
            245                 250                 255

Tyr Asn Gly Gly Pro Pro Arg Thr Cys Pro Lys Ile Lys Gln Glu Ala
            260                 265                 270

Val Ser Ser Cys Thr His Leu Gly Ala Gly Pro Pro Leu Ser Asn Gly
            275                 280                 285

His Arg Pro Ala Ala His Asp Phe Pro Leu Gly Arg Gln Leu Pro Ser
    290                 295                 300

Arg Thr Thr Pro Thr Leu Gly Leu Glu Glu Val Leu Ser Ser Arg Asp
305                 310                 315                 320

Cys His Pro Ala Leu Pro Leu Pro Pro Gly Phe His Pro His Pro Gly
                325                 330                 335

Pro Asn Tyr Pro Ser Phe Leu Pro Asp Gln Met Gln Pro Gln Val Pro
            340                 345                 350

Pro Leu His Tyr Gln Gly Gln Ser Arg Gly Phe Val Ala Arg Ala Gly
        355                 360                 365

Glu Pro Cys Val Cys Trp Pro His Phe Gly Thr His Gly Met Met Leu
    370                 375                 380

Thr Pro Pro Ser Ser Pro Leu Glu Leu Met Pro Pro Gly Ser Cys Met
385                 390                 395                 400

Pro Glu Glu Pro Lys Pro Lys Arg Gly Arg Arg Ser Trp Pro Arg Lys
                405                 410                 415

Arg Thr Ala Thr His Thr Cys Asp Tyr Ala Gly Cys Gly Lys Thr Tyr
            420                 425                 430

Thr Lys Ser Ser His Leu Lys Ala His Leu Arg Thr His Thr Gly Glu
            435                 440                 445

Lys Pro Tyr His Cys Asp Trp Asp Gly Cys Gly Trp Lys Phe Ala Arg
    450                 455                 460

Ser Asp Glu Leu Thr Arg His Tyr Arg Lys His Thr Gly His Arg Pro
465                 470                 475                 480

Phe Gln Cys Gln Lys Cys Asp Arg Ala Phe Ser Arg Ser Asp His Leu
                485                 490                 495

Ala Leu His Met Lys Arg His Phe
            500
```

<210> SEQ ID NO 6
<211> LENGTH: 1515
<212> TYPE: DNA
<213> ORGANISM: Homo sapiens

<400> SEQUENCE: 6

```
atggctgtca gcgacgcgct gctcccatct ttctccacgt tcgcgtctgg cccggcggga      60
agggagaaga cactgcgtca agcaggtgcc ccgaataacc gctggcggga ggagctctcc     120
cacatgaagc gacttccccc agtgcttccc ggccgcccct atgacctggc ggcggcgacc     180
gtggccacag acctggagag cggcggagcc ggtgcggctt cggcggtag caacctggcg      240 cccctacctc ggagagagac cgaggagttc aacgatctcc tggacctgga ctttattctc     300
tccaattcgc tgacccatcc tccggagtca gtggccgcca ccgtgtcctc gtcagcgtca     360
gcctcctctt cgtcgtcgcc gtcgagcagc ggccctgcca cgcgcgccct cacctgcagc     420
ttcacctatc cgatccgggc cgggaacgac ccgggcgtgg cgccgggcgg cacgggcgga     480
ggcctcctct atggcaggga gtccgctccc cctccgacgg ctcccttcaa cctggcggac     540
atcaacgacg tgagcccctc gggcggcttc gtggccgagc tcctgcggcc agaattggac     600
```

-continued

```
ccggtgtaca ttccgccgca gcagccgcag ccgccaggtg gcgggctgat gggcaagttc      660
gtgctgaagg cgtcgctgag cgccctggc agcgagtacg gcagcccgtc ggtcatcagc       720
gtcagcaaag gcagccctga cggcagccac ccggtggtgg tggcgcccta caacggcggg      780
ccgccgcgca cgtgccccaa gatcaagcag gaggcggtct cttcgtgcac ccacttgggc      840
gctggacccc ctctcagcaa tggccaccgg ccggctgcac acgacttccc cctggggcgg      900
cagctcccca gcaggactac cccgaccctg ggtcttgagg aagtgctgag cagcagggac      960
tgtcaccctg ccctgccgct tcctcccggc ttccatcccc acccggggcc caattaccca     1020
tccttcctgc ccgatcagat gcagccgcaa gtcccgccgc tccattacca aggtcagtcc     1080
cggggatttg tagctcgggc tggggagccc tgtgtgtgct ggccccactt cgggacacac     1140
gggatgatgc tcaccccacc ttcttcaccc ctagagctca tgccacccgg ttcctgcatg     1200
ccagaggagc ccaagccaaa gaggggaaga cgatcgtggc cccggaaaag gaccgccacc     1260
cacacttgtg attacgcggg ctgcggcaaa acctacacaa agagttccca tctcaaggca     1320
cacctgcgaa cccacacagg tgagaaacct taccactgtg actgggacgg ctgtggatgg     1380
aaattcgccc gctcagatga actgaccagg cactaccgta aacacacggg gcaccgcccg     1440
ttccagtgcc aaaaatgcga ccgagcattt tccaggtcgg accacctcgc cttacacatg     1500
aagaggcatt tttaa                                                      1515

<210> SEQ ID NO 7
<211> LENGTH: 19
<212> TYPE: DNA
<213> ORGANISM: Artificial Sequence
<220> FEATURE:
<223> OTHER INFORMATION: Forward primer for detecting klf4 gene

<400> SEQUENCE: 7
gtgccccgac taaccgttg                                                    19

<210> SEQ ID NO 8
<211> LENGTH: 20
<212> TYPE: DNA
<213> ORGANISM: Artificial Sequence
<220> FEATURE:
<223> OTHER INFORMATION: Reverse primer for detecting klf4 gene

<400> SEQUENCE: 8
gtcgttgaac tcctcggtct                                                   20

<210> SEQ ID NO 9
<211> LENGTH: 20
<212> TYPE: DNA
<213> ORGANISM: Artificial Sequence
<220> FEATURE:
<223> OTHER INFORMATION: Forward primer for detecting tox gene

<400> SEQUENCE: 9
caactcaaag ccgtcagtat                                                   20

<210> SEQ ID NO 10
<211> LENGTH: 20
<212> TYPE: DNA
<213> ORGANISM: Artificial Sequence
<220> FEATURE:
<223> OTHER INFORMATION: Reverse primer for detecting tox gene

<400> SEQUENCE: 10
gctgaggagt cattcctggt                                                   20
```

```
<210> SEQ ID NO 11
<211> LENGTH: 254
<212> TYPE: PRT
<213> ORGANISM: Artificial Sequence
<220> FEATURE:
<223> OTHER INFORMATION: anti-EpCAM scFv

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Ser
            20                  25                  30

Asn Gly Ile Thr Tyr Leu Tyr Trp Tyr Gln Gln Lys Pro Gly Lys Ala
        35                  40                  45

Pro Lys Leu Leu Ile Tyr Gln Met Ser Asn Leu Ala Ser Gly Val Pro
    50                  55                  60

Ser Arg Phe Ser Ser Ser Gly Ser Gly Thr Asp Phe Thr Leu Thr Ile
65                  70                  75                  80

Ser Ser Leu Gln Pro Glu Asp Phe Ala Thr Tyr Tyr Cys Ala Gln Asn
                85                  90                  95

Leu Glu Ile Pro Arg Thr Phe Gly Gln Gly Thr Lys Val Glu Leu Lys
            100                 105                 110

Arg Ala Thr Pro Ser His Asn Ser His Gln Val Pro Ser Ala Gly Gly
            115                 120                 125

Pro Thr Ala Asn Ser Gly Thr Ser Gly Ser Glu Val Gln Leu Val Gln
    130                 135                 140

Ser Gly Pro Gly Leu Val Gln Pro Gly Gly Ser Val Arg Ile Ser Cys
145                 150                 155                 160

Ala Ala Ser Gly Tyr Thr Phe Thr Asn Tyr Gly Met Asn Trp Val Lys
                165                 170                 175

Gln Ala Pro Gly Lys Gly Leu Glu Trp Met Gly Trp Ile Asn Thr Tyr
            180                 185                 190

Thr Gly Glu Ser Thr Tyr Ala Asp Ser Phe Lys Gly Arg Phe Thr Phe
            195                 200                 205

Ser Leu Asp Thr Ser Ala Ser Ala Ala Tyr Leu Gln Ile Asn Ser Leu
    210                 215                 220

Arg Ala Glu Asp Thr Ala Val Tyr Tyr Cys Ala Arg Phe Ala Ile Lys
225                 230                 235                 240

Gly Asp Tyr Trp Gly Gln Gly Thr Leu Leu Thr Val Ser Ser
                245                 250

<210> SEQ ID NO 12
<211> LENGTH: 45
<212> TYPE: PRT
<213> ORGANISM: Artificial Sequence
<220> FEATURE:
<223> OTHER INFORMATION: CD8 alpha hinge

<400> SEQUENCE: 12

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
            35                  40                  45
```

-continued

<210> SEQ ID NO 13
<211> LENGTH: 27
<212> TYPE: PRT
<213> ORGANISM: Artificial Sequence
<220> FEATURE:
<223> OTHER INFORMATION: CD28 transmembrane domain

<400> SEQUENCE: 13

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 14
<211> LENGTH: 112
<212> TYPE: PRT
<213> ORGANISM: Artificial Sequence
<220> FEATURE:
<223> OTHER INFORMATION: CD28 (CD

<400> SEQUENCE: 14

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 15
<211> LENGTH: 112
<212> TYPE: PRT
<213> ORGANISM: Artificial Sequence
<220> FEATURE:
<223> OTHER INFORMATION: CD3 zeta ICD

<400> SEQUENCE: 15

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 16

<211> LENGTH: 240
<212> TYPE: PRT
<213> ORGANISM: Artificial Sequence
<220> FEATURE:
<223> OTHER INFORMATION: anti-Trop-2 scFv

<400> SEQUENCE: 16

```
Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Thr Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ala Arg Gly Gly Phe Gly Ser Ser Tyr Trp Tyr Phe Asp Val Trp Gly
            100                 105                 110

Gln Gly Ser Leu Val Thr Val Ser Ser Gly Gly Gly Gly Ser Gly Gly
        115                 120                 125

Gly Gly Ser Gly Gly Gly Gly Ser Asp Ile Gln Leu Thr Gln Ser Pro
    130                 135                 140

Ser Ser Leu Ser Ala Ser Val Gly Asp Arg Val Ser Ile Thr Cys Lys
145                 150                 155                 160

Ala Ser Gln Asp Val Ser Ile Ala Val Ala Trp Tyr Gln Gln Lys Pro
                165                 170                 175

Gly Lys Ala Pro Lys Leu Leu Ile Tyr Ser Ala Ser Tyr Arg Tyr Thr
            180                 185                 190

Gly Val Pro Asp Arg Phe Ser Gly Ser Gly Ser Gly Thr Asp Phe Thr
        195                 200                 205

Leu Thr Ile Ser Ser Leu Gln Pro Glu Asp Phe Ala Val Tyr Tyr Cys
    210                 215                 220

Gln Gln His Tyr Ile Thr Pro Leu Thr Phe Gly Ala Gly Thr Lys Val
225                 230                 235                 240
```

<210> SEQ ID NO 17
<211> LENGTH: 243
<212> TYPE: PRT
<213> ORGANISM: Artificial Sequence
<220> FEATURE:
<223> OTHER INFORMATION: anti-CEACAM6 scFv

<400> SEQUENCE: 17

```
Gln Val Gln Leu Gln Glu Ser Gly Gly Gly Val Val Gln Pro Gly Arg
1               5                   10                  15

Ser Leu Arg Leu Ser Cys Ser Ser Ser Gly Phe Ala Leu Thr Asp Tyr
            20                  25                  30

Tyr Met Ser Trp Val Arg Gln Ala Pro Gly Lys Gly Leu Glu Trp Leu
        35                  40                  45

Gly Phe Ile Ala Asn Lys Ala Asn Gly His Thr Thr Asp Tyr Ser Pro
    50                  55                  60

Ser Val Lys Gly Arg Phe Thr Ile Ser Arg Asp Asn Ser Lys Asn Thr
65                  70                  75                  80

Leu Phe Leu Gln Met Asp Ser Leu Arg Pro Glu Asp Thr Gly Val Tyr
```

```
                    85                  90                  95
Phe Cys Ala Arg Asp Met Gly Ile Arg Trp Asn Phe Asp Val Trp Gly
            100                 105                 110

Gln Gly Thr Pro Val Thr Val Ser Ser Gly Gly Gly Ser Gly Gly
            115                 120                 125

Gly Gly Ser Gly Gly Gly Gly Ser Asp Ile Gln Leu Thr Gln Ser Pro
            130                 135                 140

Ser Ser Leu Ser Ala Ser Val Gly Asp Arg Val Thr Met Thr Cys Ser
145                 150                 155                 160

Ala Ser Ser Arg Val Ser Tyr Ile His Trp Tyr Gln Gln Lys Pro Gly
                165                 170                 175

Lys Ala Pro Lys Arg Trp Ile Tyr Gly Thr Ser Thr Leu Ala Ser Gly
            180                 185                 190

Val Pro Ala Arg Phe Ser Gly Ser Gly Ser Gly Thr Asp Phe Thr Phe
            195                 200                 205

Thr Ile Ser Ser Leu Gln Pro Glu Asp Ile Ala Thr Tyr Tyr Cys Gln
        210                 215                 220

Gln Trp Ser Tyr Asn Pro Pro Thr Phe Gly Gln Gly Thr Lys Val Glu
225                 230                 235                 240

Ile Lys Arg

<210> SEQ ID NO 18
<211> LENGTH: 241
<212> TYPE: PRT
<213> ORGANISM: Artificial Sequence
<220> FEATURE:
<223> OTHER INFORMATION: anti-CEACAM5 scFv

<400> SEQUENCE: 18

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Asp Phe Thr Thr Tyr
            20                  25                  30

Trp Met Ser Trp Val Arg Gln Ala Pro Gly Lys Gly Leu Glu Trp Ile
            35                  40                  45

Gly Glu Ile His Pro Asp Ser Ser Thr Ile Asn Tyr Ala Pro Ser Leu
        50                  55                  60

Lys Asp Arg Phe Thr Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Ser Leu Tyr Phe Gly Phe Pro Trp Phe Ala Tyr Trp Gly Gln Gly
            100                 105                 110

Thr Pro Val Thr Val Ser Ser Gly Gly Gly Gly Ser Gly Gly Gly Gly
            115                 120                 125

Ser Gly Gly Gly Gly Ser Asp Ile Gln Leu Thr Gln Ser Pro Ser Ser
        130                 135                 140

Leu Ser Ala Ser Val Gly Asp Arg Val Thr Ile Thr Cys Lys Ala Ser
145                 150                 155                 160

Gln Asp Val Gly Thr Ser Val Ala Trp Tyr Gln Gln Lys Pro Gly Lys
                165                 170                 175

Ala Pro Lys Leu Leu Ile Tyr Trp Thr Ser Thr Arg His Thr Gly Val
            180                 185                 190

Pro Ser Arg Phe Ser Gly Ser Gly Ser Gly Thr Asp Phe Thr Phe Thr
            195                 200                 205
```

-continued

```
Ile Ser Ser Leu Gln Pro Glu Asp Ile Ala Thr Tyr Tyr Cys Gln Gln
    210             215             220

Tyr Ser Leu Tyr Arg Ser Phe Gly Gln Gly Thr Lys Val Glu Ile Lys
225             230             235             240

Arg
```